(12) United States Patent
Hanko et al.

(10) Patent No.: US 8,536,191 B2
(45) Date of Patent: Sep. 17, 2013

(54) CRYSTALLINE AND AMORPHOUS FORMS OF NALBUPHINE HYDROCHLORIDE

(75) Inventors: Jason Hanko, West Lafayette, IN (US); Petinka Vlahova, West Lafayette, IN (US)

(73) Assignee: Noramco, Inc., Athens, GA (US)

(*) Notice: Subject to any disclaimer, the term of this patent is extended or adjusted under 35 U.S.C. 154(b) by 217 days.

(21) Appl. No.: 13/187,749

(22) Filed: Jul. 21, 2011

(65) Prior Publication Data

US 2012/0029008 A1 Feb. 2, 2012

Related U.S. Application Data

(60) Provisional application No. 61/460,741, filed on Oct. 12, 2010, provisional application No. 61/366,681, filed on Jul. 22, 2010.

(51) Int. Cl.
*A61K 31/485* (2006.01)
*C07D 489/02* (2006.01)

(52) U.S. Cl.
USPC .......................................... 514/282; 546/44

(58) Field of Classification Search
USPC .......................................... 514/282; 546/44
See application file for complete search history.

(56) References Cited

U.S. PATENT DOCUMENTS 8,173,666 B2 * 5/2012 Riggs-Sauthier et al. .... 514/282

* cited by examiner

*Primary Examiner* — Charanjit Aulakh

(57) ABSTRACT

The present invention is directed to novel crystalline and amorphous forms of nalbuphine hydrochloride.

22 Claims, 14 Drawing Sheets pXRD Pattern for nalbuphine HCl, crystalline Form A pXRD Pattern for nalbuphine HCl, crystalline Form B pXRD Pattern for nalbuphine HCl, crystalline Form C pXRD Pattern for nalbuphine HCl, crystalline Form D pXRD Pattern for nalbuphine HCl, crystalline Form F pXRD Pattern for nalbuphine HCl, crystalline Form G pXRD Pattern for nalbuphine HCl, crystalline Form H pXRD Pattern for nalbuphine HCl, crystalline Form I pXRD Pattern for nalbuphine HCl, crystalline Form K pXRD Pattern for nalbuphine HCl, crystalline Form U Moisture sorption / desorption profile, crystalline Form A Moisture sorption / desorption profile, crystalline Form B DSC profile for nalbuphine HCl, crystalline Form I DSC profile for nalbuphine HCl, crystalline Form K

CRYSTALLINE AND AMORPHOUS FORMS OF NALBUPHINE HYDROCHLORIDE

CROSS-REFERENCE TO RELATED APPLICATIONS

This application claims priority from U.S. Provisional Applications Ser. No. 61/460,741 filed Oct. 12, 2010 and Ser. No. 61/366,681, filed Jul. 22, 2010, the contents of each of which are hereby incorporated by reference in their entirety.

FIELD OF THE INVENTION

The present invention is directed to crystalline and amorphous forms of nalbuphine hydrochloride.

BACKGROUND OF THE INVENTION

Nalbuphine hydrochloride, also known as 4((−)-17-(cyclobutylmethyl)-4,5α-epoxymorphinan-3,6α,14-triol hydrochloride, ($C_{21}H_{28}ClNO_4$, MW 393.90) is a synthetic opioid agonist-antagonist analgesic of the phenanthrene series. The chemical structure of nalbuphine hydrochloride is shown below

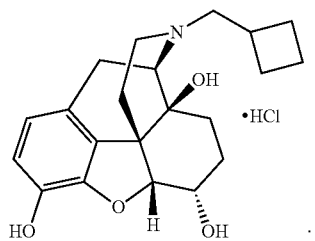 [SMILES: Oc1ccc2c3c1O[C@H]1[C@@H](O)CC[C@@]4(O)[C@@H](C2)N(CC2CCC2)CC[C@]314 ; Cl]

Nalbuphine HCl is structurally related to both the widely used opioid antagonist, naloxone, and the potent opioid analgesic, oxymorphone. Nalbuphine hydrochloride is an effective analgesic indicated for the relief of moderate to severe pain. Nalbuphine hydrochloride may also be used as a supplement to balanced anesthesia, for preoperative and postoperative analgesia, and for obstetrical analgesia during labor and delivery. Nalbuphine hydrochloride is commercially available as an injectable solution in two concentrations, more particularly in 10 mg and 20 mg of nalbuphine hydrochloride per mL.

SUMMARY OF THE INVENTION

The present invention is directed to nine novel forms of nalbuphine HCl. More particularly, the present invention is directed to eight crystalline forms of nalbuphine HCl, identified herein as Forms C, D, F, G, H, I, K, and U and an amorphous form, identified herein as Form Z. The two known crystalline forms of nalbuphine HCl are hereinafter referred to as nalbuphine HCl Form A and Form B.

The present invention is further directed to processes for the preparation of the novel crystalline and amorphous forms of nalbuphine HCl as herein defined.

Illustrative of the invention is a pharmaceutical composition comprising a pharmaceutically acceptable carrier and any of the novel crystalline or amorphous forms of nalbuphine HCl as herein defined. An illustration of the invention is a pharmaceutical composition made by mixing any of the novel crystalline or amorphous forms of nalbuphine HCl as herein defined and a pharmaceutically acceptable carrier. Illustrating the invention is a process for making a pharmaceutical composition comprising mixing any of the novel crystalline or amorphous forms of nalbuphine HCl as herein defined and a pharmaceutically acceptable carrier.

Exemplifying the invention are methods of providing analgesia, comprising administering to a subject in need thereof, a therapeutically effective amount of one or more of the novel nalbuphine HCl crystalline forms or pharmaceutical compositions described above.

DETAILED DESCRIPTION OF THE INVENTION

Figure 1:
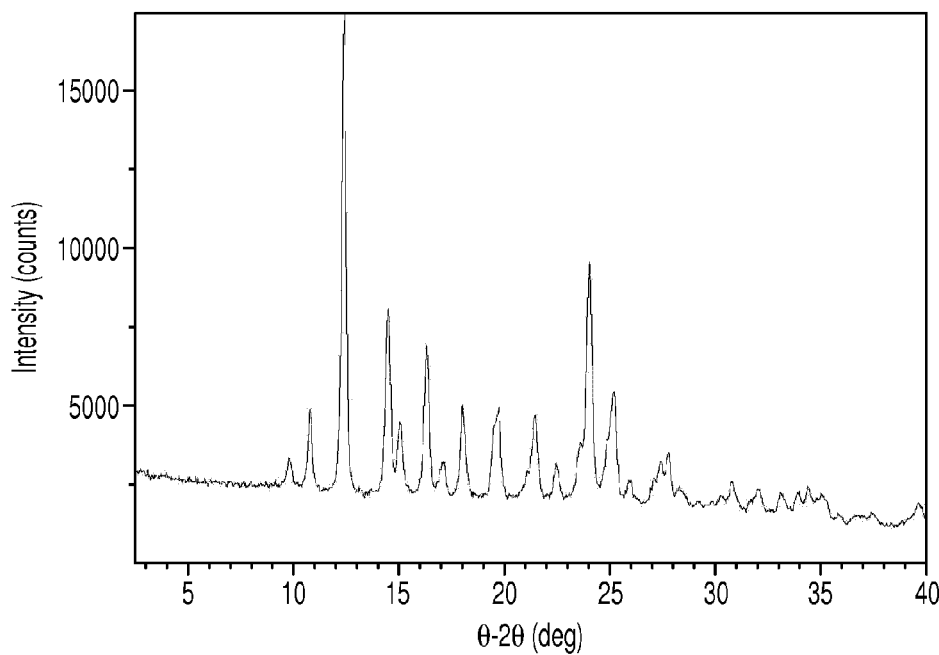
FIG. 1 illustrates a powder X-ray diffraction pattern of nalbuphine HCl crystalline Form A, expressed in terms of °2θ.

The present invention is directed to 8 novel crystalline forms of nalbuphine HCl, and 1 novel amorphous form of nalbuphine HCl, as herein described in detail. More particularly, the present invention is directed to novel crystalline forms C, D, F, G, H, I, K, and U of nalbuphine HCl, and further to the novel amorphous form Z of nalbuphine HCl.

As used herein the term "nalbuphine hydrochloride" or "nalbuphine HCl" when used alone and without modifiers, refers to the known Form A of nalbuphine hydrochloride.

The present invention is further directed to processes for the preparation of the crystalline and amorphous forms of nalbuphine HCl. In an embodiment, the crystalline or amorphous form of nalbuphine HCl is prepared from known Form A of nalbuphine HCl, as described in more detail herein.

In an embodiment, the crystalline or amorphous form of nalbuphine HCl is prepared in an isolated form. In another embodiment, the crystalline or amorphous forms of nalbuphine are prepared in a substantially pure form. In another embodiment, the crystalline or amorphous form of nalbuphine is prepared in a form which is substantially free of other novel and/or crystalline forms of nalbuphine HCl.

In an embodiment, the present invention is directed to a crystalline or amorphous form of nalbuphine HCl as herein described, wherein the crystalline or amorphous form is between about 90% and about 100% pure, preferably between about 95% and about 100% pure, more preferably between about 98% and about 100% pure.

As used herein, unless otherwise noted, the term "isolated form" shall mean that the compound is present in a form which is separate from any solid mixture with another compound(s), solvent system or biological environment. In an embodiment, the present invention is directed to crystalline forms of nalbuphine HCl as described herein, wherein said crystalline forms are present as an isolated form.

As used herein, unless otherwise noted, the term "substantially pure form" shall mean that the mole percent of impurities (including, but not limited to other crystalline forms of nalbuphine HCl, solvents, and/or other undesirable non-nalbuphine HCl impurities) in the isolated form is less than about 5 mole percent, preferably less than about 2 mole percent, more preferably, less than about 0.5 mole percent, most preferably, less than about 0.1 mole percent. In an embodiment, the present invention is directed to crystalline forms of nalbuphine HCl as described herein, wherein said crystalline forms are present as substantially pure form.

As used herein, unless otherwise noted, the term "substantially free of any other crystalline form(s)" when used to described a crystalline form of nalbuphine HCl shall mean that the mole percent of the other crystalline form(s) of nalbuphine HCl in the isolated or prepared form is less than about 10 mole percent, preferably less than about 5 mole percent, more preferably, less than about 1 mole percent, most preferably less than about 0.5 mole percent. In an embodiment, the present invention is directed to crystalline forms of nalbuphine HCl as described herein, wherein said crystalline forms are present as substantially free of any other crystalline form.

The present invention is further directed to the use of one or more of the novel crystalline forms of nabuphine HCl instead of or in combination with the Form A and/or known Form B of nalbuphine HCl for its pharmacological effect.

The present invention is further directed to a pharmaceutical composition comprising a therapeutically effective amount of one or more of the novel crystalline forms of nalbuphine HCl, alone or in combination with the known Form A and/or Form B of nalbuphine HCl. The present invention is further directed to a method of providing a therapeutic (e.g., analgesic) effect to a mammal, preferably a human, in need thereof which comprises administering to said mammal a therapeutic amount of one or more of the novel crystalline forms of nalbuphine HCl, optionally in combination with the known Form A and/or Form B of nalbuphine HCl. Nalbuphine Form A and Form B, as herein defined, are known in the art, as are therapeutic uses and dose ranges, modes of administration, etc. for said Form A of nalbuphine HCl.

As used herein, unless otherwise noted, the terms "treating", "treatment" and the like, shall include the management and care of a subject or patient (preferably mammal, more preferably human) for the purpose of combating a disease, condition, or disorder and includes the administration of a compound of the present invention to prevent the onset of the symptoms or complications, alleviate the symptoms or complications, or eliminate the disease, condition, or disorder.

As used herein, unless otherwise noted, the term "prevention" shall include (a) reduction in the frequency of one or more symptoms; (b) reduction in the severity of one or more symptoms; (c) the delay or avoidance of the development of additional symptoms; and/or (d) delay or avoidance of the development of the disorder or condition.

One skilled in the art will recognize that wherein the present invention is directed to methods of prevention, a subject in need of thereof (i.e. a subject in need of prevention) shall include any subject or patient (preferably a mammal, more preferably a human) who has experienced or exhibited at least one symptom of the disorder, disease or condition to be prevented. Further, a subject in need thereof may additionally be a subject (preferably a mammal, more preferably a human) who has not exhibited any symptoms of the disorder, disease or condition to be prevented, but who has been deemed by a physician, clinician or other medical profession to be at risk of developing said disorder, disease or condition. For example, the subject may be deemed at risk of developing a disorder, disease or condition (and therefore in need of prevention or preventive treatment) as a consequence of the subject's medical history, including, but not limited to, family history, pre-disposition, co-existing (comorbid) disorders or conditions, genetic testing, and the like.

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

Crystalline Form Details

The crystalline and amorphous Forms of nalbuphine HCl of the present invention may be prepared from known crystalline Form A of nalbuphine HCl. Examples 1-33 which follow herein, provide examples of the preparation of the crystalline and amorphous Forms of nalbuphine HCl.

The novel crystalline and amorphous forms of nalbuphine HCl may be characterized by one or more of their characteristic physical properties, including, but not limited to their powder X-ray diffraction (PXRD) peaks, single crystal unit cell parameters, crystal structure, water content (as measured by Karl-Fischer), stability to cycling temperature and/or humidity, melting point and Fourier transform infrared spectra (FT-IR).

Powder X-Ray Diffraction Measurements

The crystalline forms of nalbuphine HCl were identified by their powder X-ray diffraction (PXRD) peaks/pattern. PXRD analyses of crystalline Forms A, B, C, D, F, G, H, I, K and amorphous Form Z were performed using an Inel XRG-3000 diffractometer equipped with a CPS (Curved Position Sensitive) detector with a 2θ range of 120°. Real time data were collected using Cu—Kα radiation starting at approximately 4°2θ at a resolution of 0.03°2θ. The tube voltage and amperage were set to 40 kV and 30 mA, respectively. The monochromator slit was set at 5 mm by 160 µm. The pattern was displayed from 2.5-40°2θ. The sample was prepared for analysis by packing into a thin-walled glass capillary. The capillary was mounted onto a goniometer head that is motorized to permit spinning of the capillary during data acquisition. Instrument calibration was performed using a silicon reference standard.

PXRD analysis of crystalline Form U was performed using a Shimadzu XRD-6000 X-ray powder diffractometer using Cu Kα radiation. The instrument was equipped with a long fine focus X-ray tube. The tube voltage and amperage were set to 40 kV and 40 mA, respectively. The divergence and scattering slits were set at 1° and the receiving slit was set at 0.15 mm. Diffracted radiation was detected by a NaI scintillation detector. A θ-2θ continuous scan at 3°/min (0.4 sec/ 0.02° step) from 2.5 to 40°2θ was used. A silicon standard was analyzed to check the instrument alignment. Data were collected and analyzed using XRD-6100/7000 v. 5.0. Samples were prepared for analysis by placing them in an aluminum holder with silicon insert.

Variable-temperature X-ray powder diffraction (VT-XRPD) analysis was performed on a Shimadzu XRD-6000 X-ray powder diffractometer equipped with an Anton Paar HTK 1200 high temperature stage. The sample was packed in a ceramic holder and analyzed from 2.5 to 40°2θ at 3°/min (0.4 sec/0.02° step). The heating rate was 10° C./min. Cooling was done by shutting off the furnace. A silicon standard was analyzed to check the instrument alignment. Temperature calibration was performed using vanillin and sulfapyridine standards. Data were collected and analyzed using XRD-6100/7000 v. 5.0. In house software (Pattern Match, SSCI Inc., An Aptuit Company) was used to generate and edit the peak lists. The value of each peak position represents the value at the apex of the peak. In the tables which follow herein, the PXRD peak lists are presented for each solid form along with the conversion to 'd' value (assuming a mean Cu Kα wavelength of 1.5418 Å) and relative peak intensities scaled to 100. The relative intensity ("R.I.") of each peak is shown, wherein Relative Intensity is the ratio of the height of each peak compared to the highest peak, which is designated as 100%.

One skilled in the art will recognize that the °2θ values and the relative intensity values were generated by performing a peak search on the measured data, whereas the d-spacing values were calculated from the °2θ values, using Cu Kα mean wavelength value of λ=1.5418 Å. One skilled in the art will further recognize relative intensity for the measured peaks may vary significantly as a result of sample preparation, preferred orientation, etc. A variation of about ±20% is not atypical for these materials.

In an embodiment of the present invention, the crystalline form of nalbuphine HCl is characterized by PXRD peaks with a relative intensity of greater than about 10% and a °2θ angle of less than or equal to about 15.0°2θ. In another embodiment of the present invention, the crystalline form of nalbuphine HCl is characterized by PXRD peaks with a relative intensity of greater than about 25% and a °2θ angle of less than or equal to about 15.0°2θ. In another embodiment of the present invention, the crystalline form of nalbuphine HCl is characterized by PXRD peaks with a relative intensity of greater than about 25% and a °2θ angle of less than or equal to about 12.0°2θ

Nalbuphine HCl Crystalline Form A

The PXRD spectrum for a representative sample of nalbuphine HCl crystalline Form A was collected and analyzed. Crystalline Form A may be characterized by its PXRD peaks, as listed in Table A, below. FIG. 1 illustrates a representative PXRD pattern for a representative sample of nalbuphine HCl crystalline form A.

TABLE A1

PXRD Peaks, Crystalline Form A

| Position °2θ (±0.01) | d-spacing Å | Relative Intensity (%) |
|---|---|---|
| 9.78 | 9.044 | 19 |
| 10.77 | 8.214 | 28 |
| 12.42 | 7.127 | 100 |
| 14.49 | 6.113 | 47 |
| 15.06 | 5.883 | 26 |
| 16.32 | 5.431 | 40 |
| 17.10 | 5.185 | 19 |
| 18.03 | 4.920 | 29 |
| 19.71 | 4.504 | 29 |
| 21.42 | 4.148 | 27 |
| 22.47 | 3.957 | 18 |
| 24.03 | 3.703 | 55 |
| 25.17 | 3.538 | 31 |
| 25.89 | 3.441 | 15 |
| 27.42 | 3.253 | 19 |
| 27.75 | 3.215 | 20 |
| 30.78 | 2.905 | 15 |
| 32.07 | 2.791 | 14 |
| 33.09 | 2.707 | 13 |
| 33.96 | 2.640 | 13 |

Nalbuphine HCl, crystalline Form A may be characterized by its powder XRD pattern which comprises peaks having a relative intensity of greater than or equal to about 20%, preferably peaks having a relative intensity of greater than or equal to about 40%.

Nalbuphine HCl, crystalline Form A may alternatively be characterized by its PXRD pattern which comprises the following characteristic peaks, as listed in Table A2, below. The characteristic peaks represent a special subset of the Form A PXRD peaks that as a group and in specific combinations of peak pairs and peak triplets are specific to Form A and no other crystalline form of nalbuphine HCl.

TABLE A2

Characteristic PXRD peaks, Form A

| Position °2θ | d-spacing (Å) | overlaps with |
|---|---|---|
| 9.78 ± 0.10 | 9.044 | C, K, H |
| 15.06 ± 0.10 | 5.883 | B, C, D |
| 21.42 ± 0.10 | 4.148 | C, D, H |

Nalbuphine HCl Crystalline Form B

Figure 2:
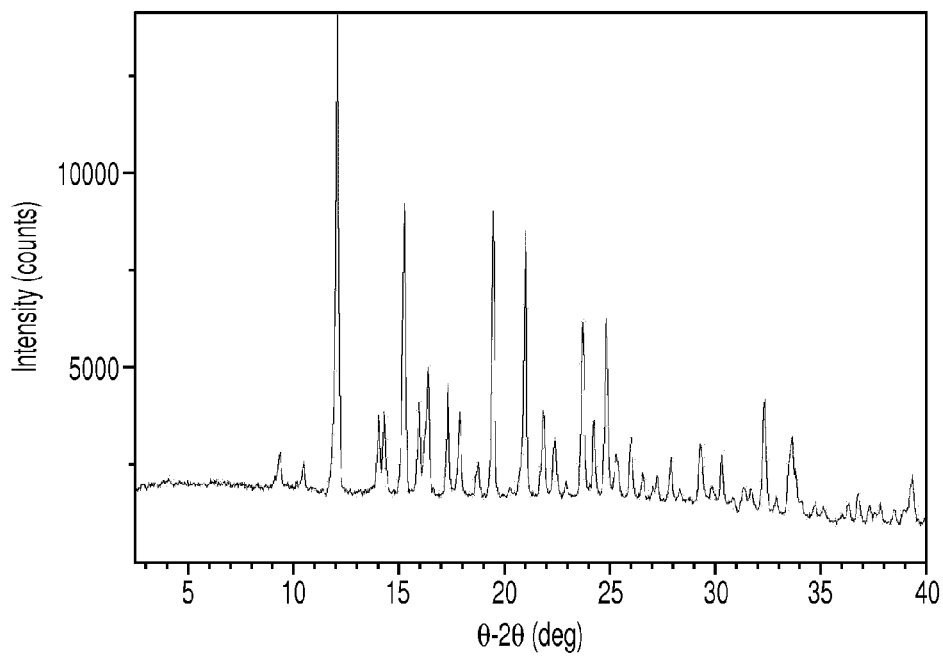
FIG. 2 illustrates a powder X-ray diffraction pattern of nalbuphine HCl crystalline Form B, expressed in terms of °2θ.

The PXRD spectra for a representative sample of nalbuphine HCl crystalline Form B was collected and analyzed. Crystalline Form B may be characterized by its PXRD peaks, as listed in Table B1, below. FIG. 2 illustrates a representative PXRD pattern for a representative sample of nalbuphine HCl crystalline form B.

TABLE B1

PXRD Peaks, Crystalline Form B

| Position °2θ (±0.01) | d-spacing Å | Relative Intensity (%) |
|---|---|---|
| 9.40 | 9.408 | 19 |
| 10.54 | 8.393 | 18 |
| 12.10 | 7.314 | 100 |
| 14.05 | 6.303 | 26 |
| 14.35 | 6.172 | 27 |
| 15.28 | 5.798 | 54 |
| 15.97 | 5.549 | 29 |
| 16.42 | 5.398 | 35 |
| 17.35 | 5.111 | 21 |
| 17.92 | 4.950 | 27 |
| 18.79 | 4.722 | 18 |
| 19.51 | 4.550 | 61 |
| 21.01 | 4.228 | 59 |
| 21.88 | 4.062 | 27 |
| 22.42 | 3.965 | 23 |
| 23.74 | 3.748 | 43 |
| 24.28 | 3.666 | 26 |
| 24.85 | 3.583 | 44 |
| 25.33 | 3.516 | 19 |
| 26.02 | 3.424 | 22 |
| 27.91 | 3.197 | 19 |
| 29.32 | 3.046 | 21 |
| 30.31 | 2.949 | 20 |
| 32.35 | 2.767 | 29 |

Nalbuphine HCl, crystalline Form B may characterized by its powder XRD pattern which comprises peaks having a relative intensity of greater than or equal to about 20%, preferably peaks having a relative intensity of greater than or equal to about 40%.

Nalbuphine HCl, crystalline Form B may alternatively be characterized by its PXRD pattern which comprises the following characteristic peaks, as listed in Table B2, below.

TABLE B2

Characteristic PXRD peaks, Form B

| Position °2θ | d-spacing (Å) | overlaps with |
|---|---|---|
| 9.40 ± 0.10 | 9.408 | None |
| 10.54 ± 0.10 | 8.393 | F |
| 12.10 ± 0.10 | 7.314 | C, D, G, U |
| 14.05 ± 0.10 | 6.303 | D, F |

Nalbuphine HCl Crystalline Form C

Figure 3:
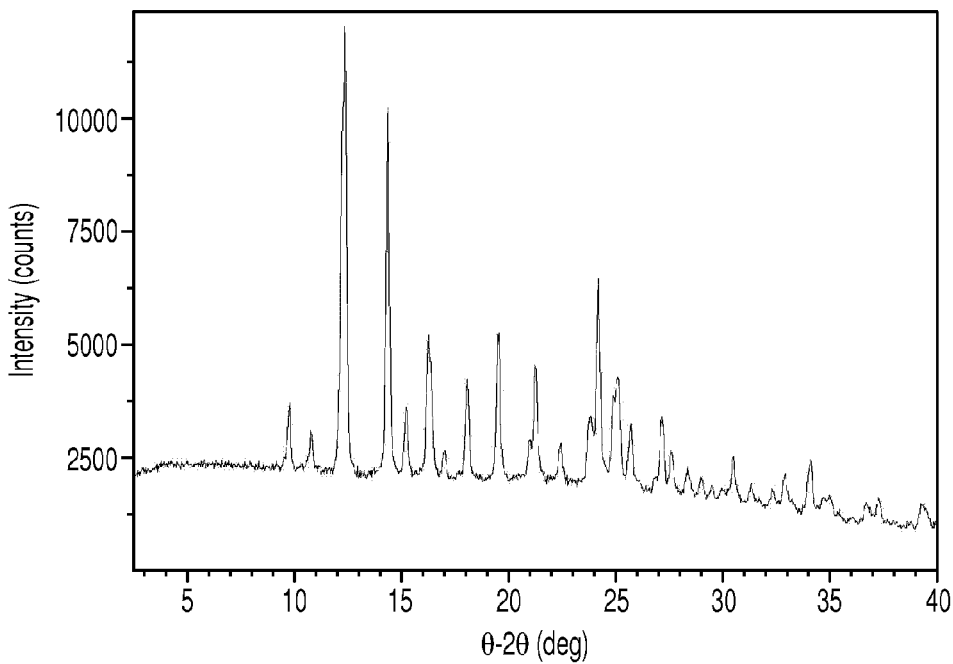
FIG. 3 illustrates a powder X-ray diffraction pattern of nalbuphine HCl crystalline Form C, expressed in terms of °2θ.

The PXRD spectra for a representative sample of nalbuphine HCl crystalline Form C was collected and analyzed. Crystalline Form C may be characterized by its PXRD peaks, as listed in Table C1, below. FIG. 3 illustrates a representative PXRD pattern for a representative sample of nalbuphine HCl crystalline form C.

TABLE C1

PXRD Peaks, Crystalline Form C

| Position °2θ (±0.01) | d-spacing Å | Relative Intensity (%) |
|---|---|---|
| 9.76 | 9.062 | 30 |
| 10.75 | 8.230 | 25 |
| 12.37 | 7.155 | 100 |
| 14.35 | 6.172 | 83 |
| 15.22 | 5.821 | 29 |
| 16.27 | 5.448 | 42 |
| 16.99 | 5.219 | 22 |
| 18.07 | 4.909 | 35 |
| 19.51 | 4.550 | 43 |
| 21.25 | 4.181 | 37 |
| 22.42 | 3.965 | 23 |
| 23.8 | 3.739 | 28 |
| 24.19 | 3.679 | 53 |
| 25.09 | 3.549 | 35 |
| 25.69 | 3.468 | 27 |
| 27.13 | 3.287 | 28 |
| 27.58 | 3.234 | 22 |
| 30.49 | 2.932 | 21 |
| 32.89 | 2.723 | 18 |
| 34.06 | 2.632 | 20 |

In an embodiment, crystalline Form C is characterized by its powder XRD pattern which comprises peaks having a relative intensity of greater than or equal to about 20%, preferably peaks having a relative intensity of greater than or equal to about 40%.

In another embodiment, nalbuphine HCl, crystalline Form C is characterized by its PXRD pattern which comprises the following characteristic peaks, as listed in Table C2, below.

TABLE C2

Characteristic PXRD peaks, Form C

| Position °2θ | d-spacing (Å) | overlaps with |
|---|---|---|
| 9.76 ± 0.10 | 9.062 | A, H |
| 15.22 ± 0.10 | 5.821 | A, B, G, H, K |
| 19.51 ± 0.10 | 4.550 | A, B, D |

Nalbuphine HCl Crystalline Form D

Figure 4:
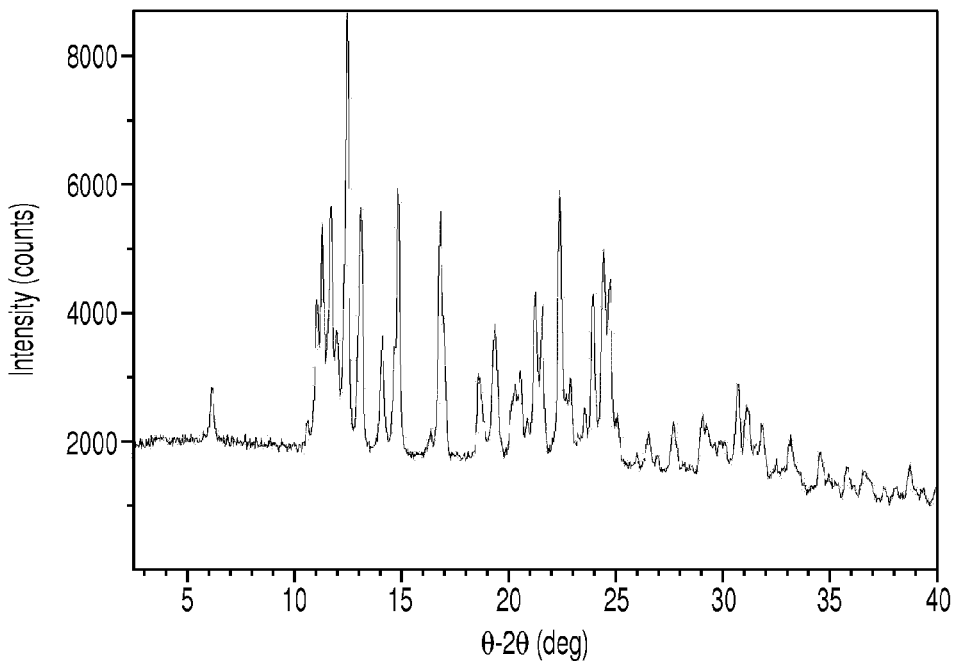
FIG. 4 illustrates a powder X-ray diffraction pattern of nalbuphine HCl crystalline Form D, expressed in terms of °2θ.

The PXRD spectra for a representative sample of nalbuphine HCl crystalline Form D was collected and analyzed. Crystalline Form D may be characterized by its PXRD peaks, as listed in Table D1, below. FIG. 4 illustrates a representative PXRD pattern for a representative sample of nalbuphine HCl crystalline form D.

TABLE D1

PXRD Peaks, Crystalline Form D

| Position °2θ (±0.01) | d-spacing Å | Relative Intensity (%) |
|---|---|---|
| 6.22 | 14.209 | 33 |
| 11.11 | 7.964 | 49 |
| 11.35 | 7.796 | 62 |
| 11.77 | 7.519 | 66 |
| 12.52 | 7.070 | 100 |
| 13.15 | 6.733 | 65 |
| 14.17 | 6.250 | 43 |
| 14.89 | 5.949 | 69 |
| 16.87 | 5.255 | 65 |

TABLE D1-continued

PXRD Peaks, Crystalline Form D

| Position °2θ (±0.01) | d-spacing Å | Relative Intensity (%) |
|---|---|---|
| 18.64 | 4.760 | 36 |
| 19.39 | 4.578 | 44 |
| 20.59 | 4.314 | 36 |
| 21.28 | 4.175 | 50 |
| 21.61 | 4.112 | 48 |
| 22.45 | 3.960 | 68 |
| 23.98 | 3.711 | 50 |
| 24.49 | 3.635 | 58 |
| 27.76 | 3.214 | 26 |
| 29.11 | 3.068 | 28 |
| 30.73 | 2.909 | 34 |

In an embodiment, crystalline Form D is characterized by its powder XRD pattern which comprises peaks having a relative intensity of greater than or equal to about 35%, preferably peaks having a relative intensity of greater than or equal to about 50%.

In another embodiment, nalbuphine HCl, crystalline Form D is characterized by its PXRD pattern which comprises the following characteristic peaks, as listed in Table D2, below.

TABLE D2

Characteristic PXRD peaks, Form D

| Position °2θ | d-spacing (Å) | overlaps with |
|---|---|---|
| 6.22 ± 0.10 | 14.209 | None |
| 11.11 ± 0.10 | 7.964 | G, H |
| 13.15 ± 0.10 | 6.733 | G, U |
| 14.89 ± 0.10 | 5.949 | None |

Nalbuphine HCl Crystalline Form F

Figure 5:
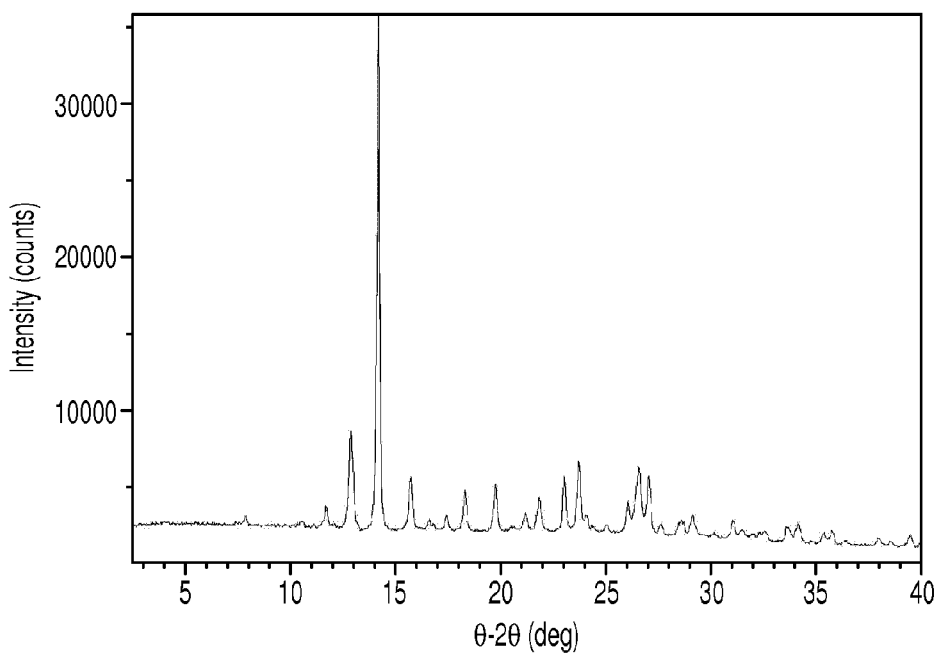
FIG. 5 illustrates a powder X-ray diffraction pattern of nalbuphine HCl crystalline Form F, expressed in terms of °2θ.

The PXRD spectra for a representative sample of nalbuphine HCl crystalline Form F was collected and analyzed. Crystalline Form F may be characterized by its PXRD peaks, as listed in Table F1, below. FIG. 5 illustrates a representative PXRD pattern for a representative sample of nalbuphine HCl crystalline form F.

TABLE F1

PXRD Peaks, Crystalline Form F

| Position °2θ (±0.01) | d-spacing Å | Relative Intensity (%) |
|---|---|---|
| 7.89 | 11.205 | 9 |
| 10.59 | 8.354 | 8 |
| 11.73 | 7.544 | 11 |
| 12.90 | 6.862 | 25 |
| 14.22 | 6.228 | 100 |
| 15.75 | 5.627 | 16 |
| 16.62 | 5.334 | 8 |
| 17.46 | 5.079 | 9 |
| 18.33 | 4.840 | 13 |
| 19.77 | 4.491 | 15 |
| 21.21 | 4.189 | 9 |
| 21.87 | 4.064 | 12 |
| 23.07 | 3.855 | 16 |
| 23.76 | 3.745 | 18 |
| 25.05 | 3.555 | 7 |
| 26.07 | 3.418 | 12 |
| 26.58 | 3.353 | 18 |
| 27.06 | 3.295 | 16 |
| 27.63 | 3.228 | 7 |
| 29.13 | 3.065 | 9 |

In an embodiment, crystalline Form F is characterized by its powder XRD pattern which comprises peaks having a relative intensity of greater than or equal to about 10%, preferably peaks having a relative intensity of greater than or equal to about 15%.

In another embodiment, nalbuphine HCl, crystalline Form F is characterized by its PXRD pattern which comprises the following characteristic peaks, as listed in Table F2, below.

TABLE F2

Characteristic PXRD peaks, Form F

| Position °2θ | d-spacing (Å) | overlaps with |
|---|---|---|
| 7.89 ± 0.10 | 11.205 | G |
| 12.90 ± 0.10 | 6.862 | U |
| 14.22 ± 0.10 | 6.228 | B, C, D, H |
| 15.75 ± 0.10 | 5.627 | G |

Nalbuphine HCl Crystalline Form G

Figure 6:
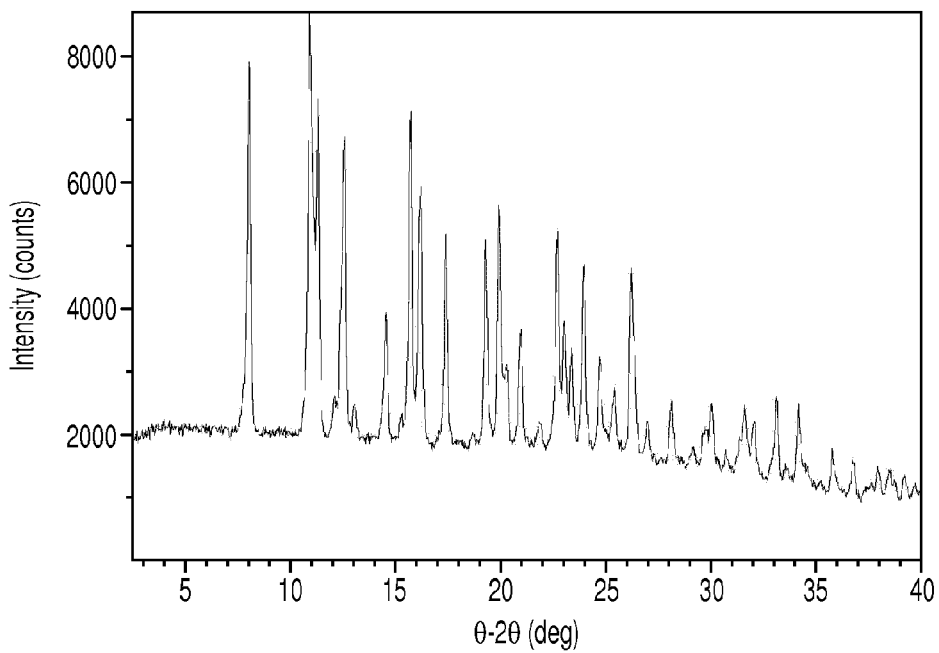
FIG. 6 illustrates a powder X-ray diffraction pattern of nalbuphine HCl crystalline Form G, expressed in terms of °2θ.

The PXRD spectra for a representative sample of nalbuphine HCl crystalline Form G was collected and analyzed. Crystalline Form G may be characterized by its PXRD peaks, as listed in Table G1, below. FIG. 6 illustrates a representative PXRD pattern for a representative sample of nalbuphine HCl crystalline form G.

TABLE G1

PXRD Peaks, Crystalline Form G

| Position °2θ (±0.01) | d-spacing Å | Relative Intensity (%) |
|---|---|---|
| 8.05 | 10.983 | 92 |
| 10.93 | 8.094 | 100 |
| 11.32 | 7.816 | 86 |
| 12.55 | 7.053 | 77 |
| 14.56 | 6.084 | 45 |
| 15.70 | 5.644 | 81 |
| 16.21 | 5.468 | 70 |
| 17.41 | 5.094 | 61 |
| 19.27 | 4.606 | 58 |
| 19.93 | 4.455 | 65 |
| 20.95 | 4.240 | 43 |
| 22.69 | 3.919 | 61 |
| 23.02 | 3.863 | 44 |
| 23.38 | 3.805 | 40 |
| 23.95 | 3.715 | 55 |
| 24.70 | 3.604 | 38 |
| 25.42 | 3.504 | 32 |
| 26.23 | 3.397 | 54 |
| 28.12 | 3.173 | 30 |
| 30.04 | 2.975 | 29 |
| 33.13 | 2.704 | 30 |
| 34.15 | 2.625 | 29 |

In an embodiment, crystalline Form G is characterized by its powder XRD pattern which comprises peaks having a relative intensity of greater than or equal to about 35%, preferably peaks having a relative intensity of greater than or equal to about 50%.

In another embodiment, nalbuphine HCl, crystalline Form G is characterized by its PXRD pattern which comprises the following characteristic peaks, as listed in Table G2, below.

TABLE G2

Characteristic PXRD peaks, Form G

| Position °2θ | d-spacing (Å) | overlaps with |
|---|---|---|
| 8.05 ± 0.10 | 10.983 | None |
| 10.93 ± 0.10 | 8.094 | A, I, K, U |
| 11.32 ± 0.10 | 7.816 | D, H |
| 15.70 ± 0.10 | 5.644 | F, I |
| 17.41 ± 0.10 | 5.094 | B, F |

Nalbuphine HCl Crystalline Form H

Figure 7:
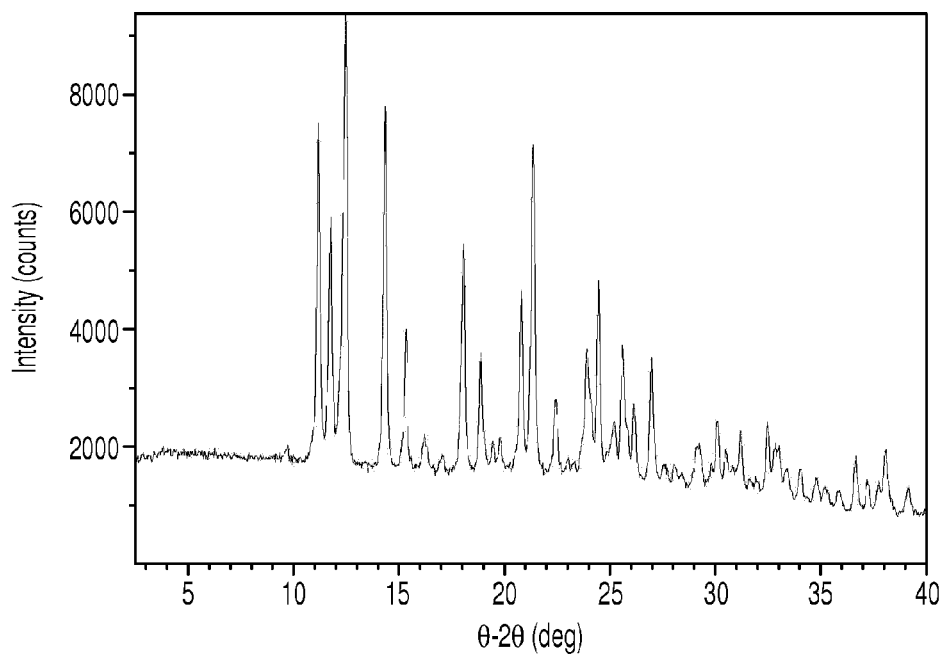
FIG. 7 illustrates a powder X-ray diffraction pattern of nalbuphine HCl crystalline Form H, expressed in terms of °2θ.

The PXRD spectra for a representative sample of nalbuphine HCl crystalline Form H was collected and analyzed. Crystalline Form H may be characterized by its PXRD peaks, as listed in Table H1, below. FIG. 7 illustrates a representative PXRD pattern for a representative sample of nalbuphine HCl crystalline form H.

TABLE H1

PXRD Peaks, Crystalline Form H

| Position °2θ (±0.01) | d-spacing Å | Relative Intensity (%) |
|---|---|---|
| 11.23 | 7.879 | 79 |
| 11.80 | 7.500 | 63 |
| 12.52 | 7.070 | 100 |
| 14.38 | 6.159 | 84 |
| 15.37 | 5.765 | 43 |
| 18.10 | 4.901 | 58 |
| 18.91 | 4.693 | 39 |
| 20.83 | 4.264 | 49 |
| 21.40 | 4.152 | 77 |
| 22.48 | 3.955 | 30 |
| 23.95 | 3.715 | 39 |
| 24.49 | 3.635 | 52 |
| 25.24 | 3.528 | 26 |
| 25.63 | 3.476 | 40 |
| 26.17 | 3.405 | 29 |
| 27.01 | 3.301 | 38 |
| 30.13 | 2.966 | 26 |
| 31.24 | 2.863 | 24 |
| 32.50 | 2.755 | 26 |
| 36.67 | 2.451 | 20 |
| 38.11 | 2.361 | 21 |

In an embodiment, crystalline Form H is characterized by its powder XRD pattern which comprises peaks having a relative intensity of greater than or equal to about 25%, preferably peaks having a relative intensity of greater than or equal to about 40%.

In another embodiment, nalbuphine HCl, crystalline Form H is characterized by its PXRD pattern which comprises the following characteristic peaks, as listed in Table H2, below.

TABLE H2

Characteristic PXRD peaks, Form H

| Position °2θ | d-spacing (Å) | overlaps with |
|---|---|---|
| 11.23 ± 0.10 | 7.879 | D, G |
| 15.37 ± 0.10 | 5.765 | B, G, K |
| 18.91 ± 0.10 | 4.693 | B, U |

Nalbuphine HCl Crystalline Form I

Figure 8:
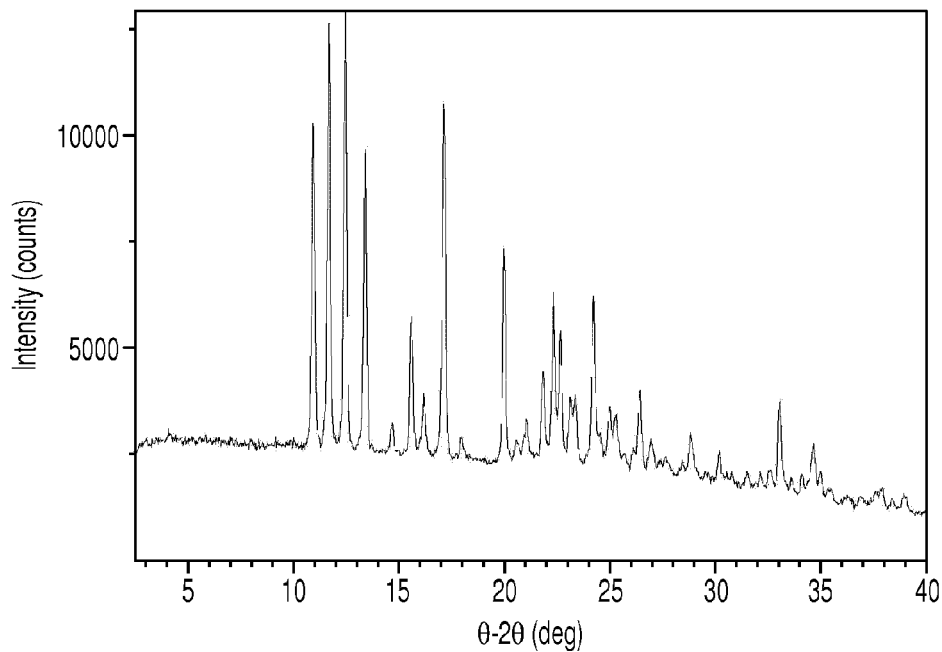
FIG. 8 illustrates a powder X-ray diffraction pattern of nalbuphine HCl crystalline Form I, expressed in terms of °2θ.

The PXRD spectra for a representative sample of nalbuphine HCl crystalline Form I was collected and analyzed. Crystalline Form I may be characterized by its PXRD peaks, as listed in Table I1, below. FIG. 8 illustrates a representative PXRD pattern for a representative sample of nalbuphine HCl crystalline form I.

TABLE I1

PXRD Peaks, Crystalline Form I

| Position °2θ (±0.01) | d-spacing Å | Relative Intensity (%) |
|---|---|---|
| 10.89 | 8.124 | 78 |
| 11.64 | 7.602 | 94 |
| 12.45 | 7.109 | 100 |
| 13.38 | 6.617 | 75 |
| 14.64 | 6.051 | 25 |
| 15.57 | 5.691 | 44 |
| 16.17 | 5.481 | 30 |
| 17.10 | 5.185 | 82 |
| 17.94 | 4.944 | 22 |
| 19.95 | 4.450 | 54 |
| 21.00 | 4.230 | 26 |
| 21.81 | 4.075 | 34 |
| 22.29 | 3.988 | 48 |
| 22.62 | 3.931 | 41 |
| 23.10 | 3.850 | 29 |
| 24.18 | 3.681 | 48 |
| 24.96 | 3.567 | 28 |
| 26.40 | 3.376 | 31 |
| 28.80 | 3.100 | 23 |
| 33.03 | 2.712 | 29 |
| 34.62 | 2.591 | 21 |

In an embodiment, crystalline Form I is characterized by its powder XRD pattern which comprises peaks having a relative intensity of greater than or equal to about 20%, preferably peaks having a relative intensity of greater than or equal to about 40%.

In another embodiment, nalbuphine HCl, crystalline Form I is characterized by its PXRD pattern which comprises the following characteristic peaks, as listed in Table 12, below.

TABLE I2

Characteristic PXRD peaks, Form I

| Position °2θ | d-spacing (Å) | overlaps with |
|---|---|---|
| 11.64 ± 0.10 | 7.602 | D, F, H, K |
| 13.38 ± 0.10 | 6.617 | K, U |
| 14.64 ± 0.10 | 6.051 | A, G |
| 15.57 ± 0.10 | 5.691 | G |

Nalbuphine HCl Crystalline Form K

Figure 9:
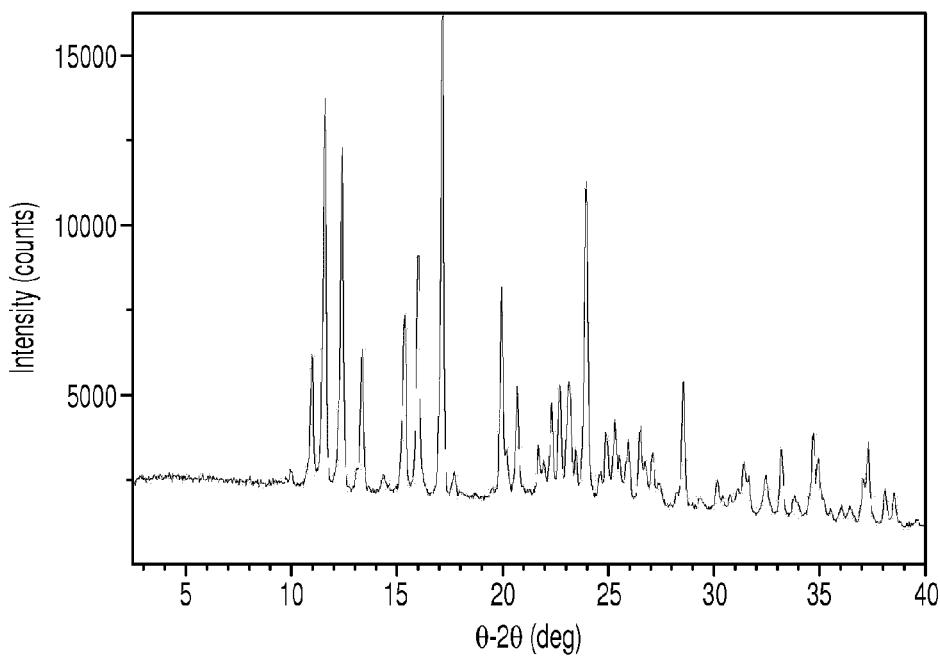
FIG. 9 illustrates a powder X-ray diffraction pattern of nalbuphine HCl crystalline Form K, expressed in terms of °2θ.

The PXRD spectra for a representative sample of nalbuphine HCl crystalline Form K was collected and analyzed. Crystalline Form K may be characterized by its PXRD peaks, as listed in Table K1, below. FIG. 9 illustrates a representative PXRD pattern for a representative sample of nalbuphine HCl crystalline form K.

TABLE K1

PXRD Peaks, Crystalline Form K

| Position °2θ (±0.01) | d-spacing Å | Relative Intensity (%) |
|---|---|---|
| 10.98 | 8.058 | 38 |
| 11.58 | 7.642 | 84 |
| 12.42 | 7.127 | 75 |
| 13.35 | 6.632 | 39 |
| 15.36 | 5.768 | 45 |
| 15.99 | 5.543 | 57 |
| 17.13 | 5.176 | 100 |
| 19.95 | 4.450 | 49 |
| 20.70 | 4.291 | 32 |
| 22.32 | 3.983 | 30 |
| 22.71 | 3.915 | 32 |
| 23.13 | 3.845 | 33 |
| 23.94 | 3.717 | 69 |
| 24.90 | 3.576 | 24 |
| 25.29 | 3.522 | 26 |
| 25.92 | 3.437 | 23 |
| 26.52 | 3.361 | 25 |
| 27.09 | 3.292 | 20 |

TABLE K1-continued

PXRD Peaks, Crystalline Form K

| Position °2θ (±0.01) | d-spacing Å | Relative Intensity (%) |
|---|---|---|
| 28.56 | 3.125 | 34 |
| 32.46 | 2.758 | 16 |
| 33.18 | 2.700 | 21 |
| 34.68 | 2.587 | 24 |
| 37.29 | 2.411 | 22 |

In an embodiment, crystalline Form K is characterized by its powder XRD pattern which comprises peaks having a relative intensity of greater than or equal to about 20%, preferably peaks having a relative intensity of greater than or equal to about 40%.

In another embodiment, nalbuphine HCl, crystalline Form K is characterized by its PXRD pattern which comprises the following characteristic peaks, as listed in Table K2, below.

TABLE K2

Characteristic PXRD peaks, Form K

| Position °2θ | d-spacing (Å) | overlaps with |
|---|---|---|
| 10.98 ± 0.10 | 8.058 | D, G, I, U |
| 11.58 ± 0.10 | 7.642 | D, F, I |
| 13.35 ± 0.10 | 6.632 | I, U |
| 15.36 ± 0.10 | 5.768 | B, C, G, H |

Nalbuphine HCl Crystalline Form U

Figure 10:
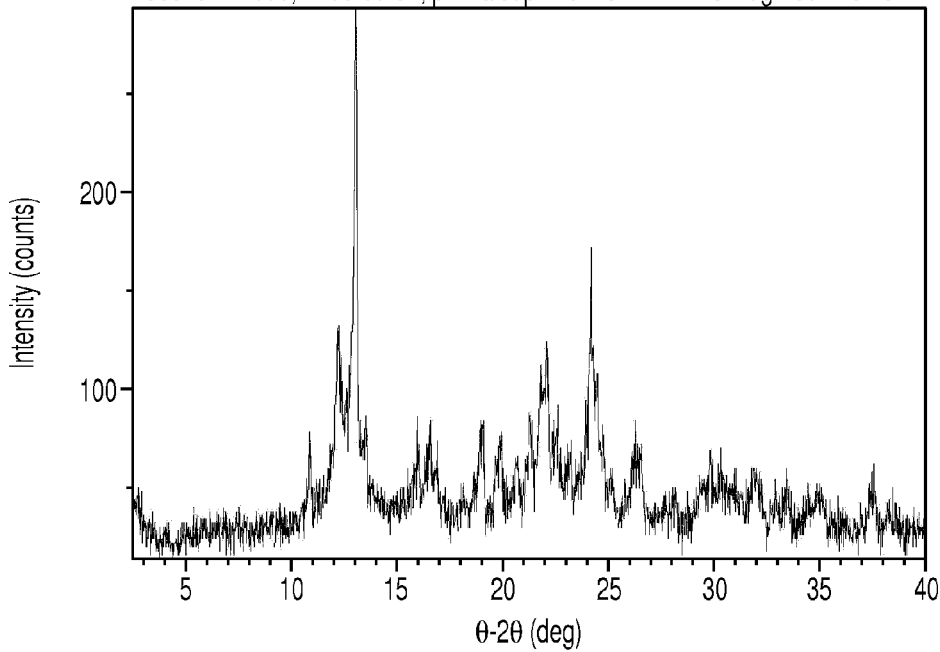
FIG. 10 illustrates a powder X-ray diffraction pattern of nalbuphine HCl crystalline Form U, expressed in terms of °2θ.
Figure 11:
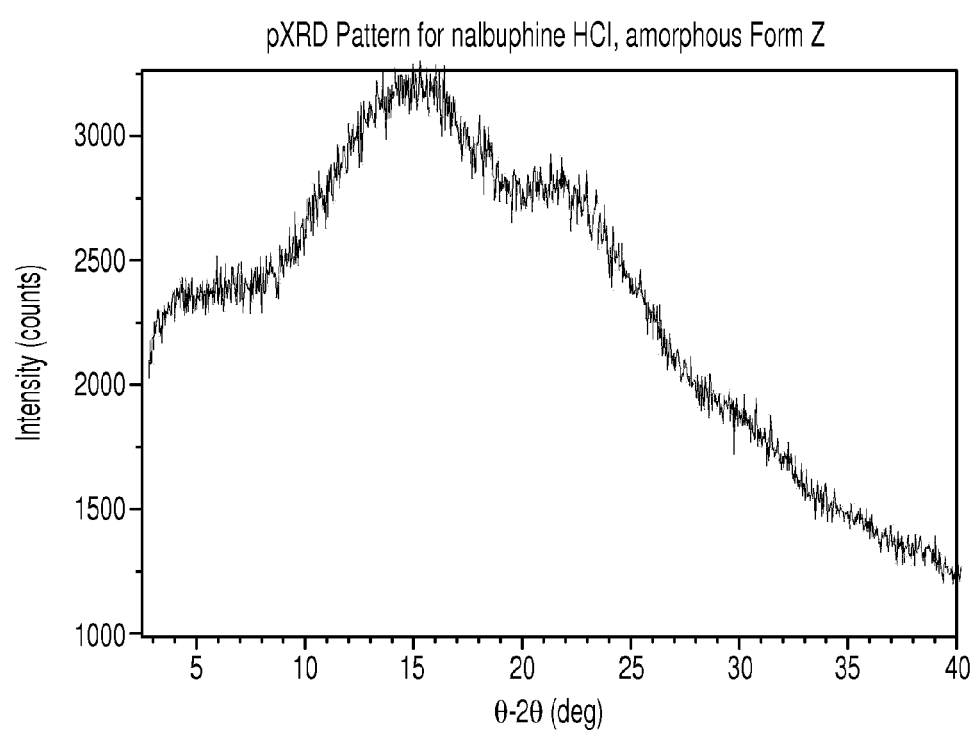
FIG. 11 illustrates a powder X-ray diffraction pattern of nalbuphine HCl amorphous Form Z, expressed in terms of °2θ.
Figure 12:
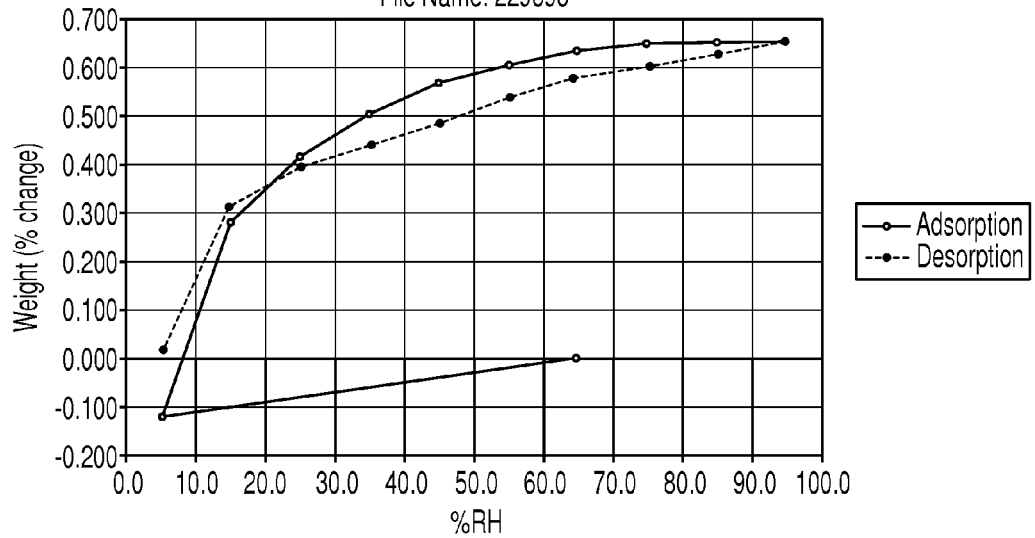
FIG. 12 illustrates an automated moisture sorption/desorption profile for nalbuphine HCl crystalline Form A.
Figure 13:
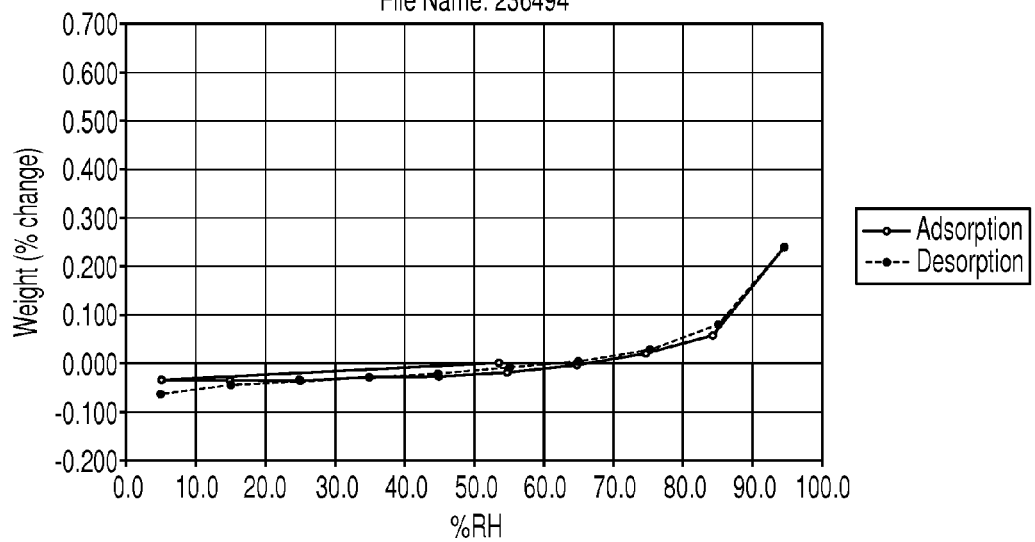
FIG. 13 illustrates an automated moisture sorption/desorption profile for nalbuphine HCl crystalline Form B.
Figure 14:
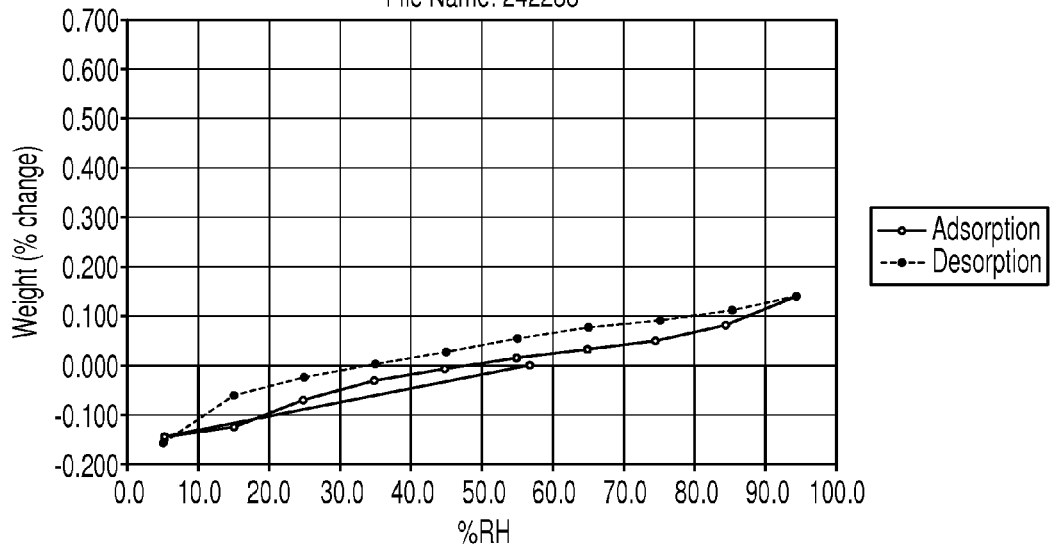
FIG. 14 illustrates an automated moisture sorption/desorption profile for nalbuphine HCl crystalline Form C.
Figure 15:
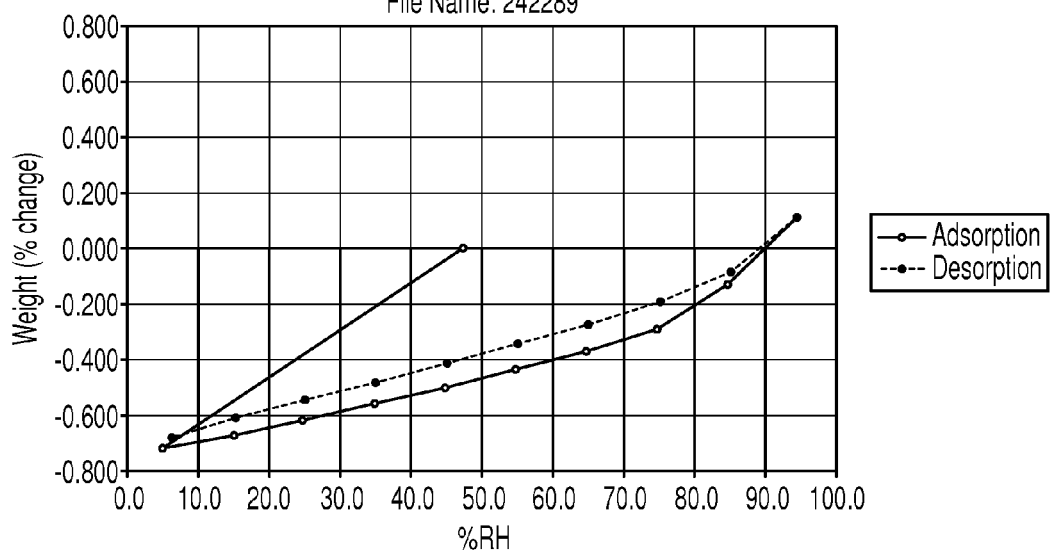
FIG. 15 illustrates an automated moisture sorption/desorption profile for nalbuphine HCl crystalline Form D.
Figure 16:
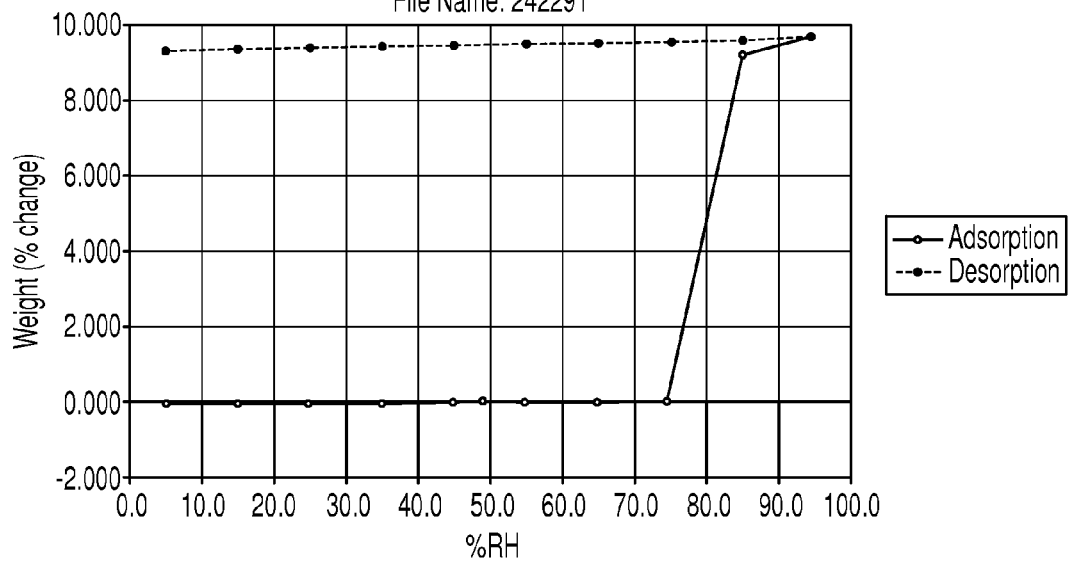
FIG. 16 illustrates an automated moisture sorption/desorption profile for nalbuphine HCl crystalline Form F.

The PXRD spectra for a representative sample of nalbuphine HCl crystalline Form U was collected and analyzed. Crystalline Form U may be characterized by its PXRD peaks, as listed in Table U1, below. FIG. 10 illustrates a representative PXRD pattern for a representative sample of nalbuphine HCl crystalline form U.

TABLE U1

PXRD Peaks, Crystalline Form U

| Postion °2θ (±0.01) | d-spacing Å | Relative Intensity (%) |
|---|---|---|
| 10.88 | 8.132 | 16 |
| 12.18 | 7.266 | 44 |
| 13.04 | 6.789 | 100 |
| 13.52 | 6.549 | 21 |
| 15.98 | 5.546 | 16 |
| 16.54 | 5.359 | 24 |
| 19.04 | 4.661 | 24 |
| 19.90 | 4.462 | 21 |
| 20.64 | 4.303 | 17 |
| 21.26 | 4.179 | 26 |
| 21.80 | 4.077 | 30 |
| 22.08 | 4.026 | 26 |
| 22.58 | 3.938 | 16 |
| 24.16 | 3.684 | 56 |
| 25.16 | 3.539 | 11 |
| 26.26 | 3.394 | 25 |
| 37.56 | 2.395 | 17 |

In an embodiment, crystalline Form U is characterized by its powder XRD pattern which comprises peaks having a relative intensity of greater than or equal to about 15%, preferably peaks having a relative intensity of greater than or equal to about 25%.

In another embodiment, nalbuphine HCl, crystalline Form U is characterized by its PXRD pattern which comprises the following characteristic peaks, as listed in Table U2, below.

TABLE U2

Characteristic PXRD peaks, Form U

| Position °2θ | d-spacing (Å) | overlaps with |
|---|---|---|
| 12.18 ± 0.10 | 7.266 | B |
| 13.04 ± 0.10 | 6.789 | D, F |
| 13.52 ± 0.10 | 6.549 | I, K |
| 19.04 ± 0.10 | 4.661 | H |

Single Crystal Structure Determination

Single crystal structure solution of crystalline Form B is disclosed in the literature (R. J. Sime, M. Dobler, R. L. Sime *Acta Crystallogr*, B: *Struct. Crystallogr. Cryst. Chem.*, 1976, 32, 809). Additionally, the single crystal structure of Form H was solved. For other solid forms where single crystal data was not available, indexing was carried out to solve the structure.

Powder X-Ray Diffraction Pattern Indexing

The PXRD patterns for the nalbuphine HCl crystalline forms were subjected to indexing using Dicvol (Dicvol v6.0 Oct. 2006—D. Louer, A. Boultif). Indexing makes use of a peak list generated from measured powder X-ray diffraction patterns to calculate a crystal unit cell consistent with the peak list. As a result of indexing, each peak is associated with a Miller index (hkl) corresponding to the crystalline planes responsible for the peak. The ability to index a measured powder X-ray diffraction pattern and arrive at a unit cell whose volume is consistent with the molecular entity is consider to be proof that the measured PXRD data represents a single phase crystalline form. During the indexing, the initial long peak list is reduced to a smaller list of peaks that still indexes to the same unit cell.

Unit cell refinement was employed whenever a number of well defined diffraction peaks from a particular crystalline solid form were observed in a powder pattern. The observed peaks were initially provided with a Miller Index according to a look-up table, which has been defined by either single crystal analysis or through indexing. Using the observe peak positions and the associated Miller Indices, the unit cell refinement program derived the 'best' unit cell that described the observed peak positions.

Performing indexing on the measured powder patterns and using the unit cell values from the two known crystal structures allowed the assignment of Miller Indices to the measured peaks for Forms A, B, and C. Forms A, B and C have very similar crystalline structure. This allows the use of the known Form B crystal structure to assign a self consistent set of Miller indices for all three forms.

In the following tables, peak positions and associated Miller Indices are presented for the most characteristic peaks for Forms A, B, and C. The allocation of Miller Indices allows each measured peak to be associated with specific crystalline planes within the sample. The Miller indices are then used to assign measured peaks into families of reflections generated by the same crystal lattice planes. Because each peak family is associated with the same crystalline planes, the separation between the peaks in the measured data is a constant for a specific crystalline form.

Nalbuphine Crystalline Form B

The single crystal structure of Form B is known. The measured crystal structure is orthorhombic P212121 with unit cell parameters of a=11.576 Å, b=12.336 Å, c=14.658 Å and with a volume=2093.2 Å$^3$. Indexing the measured peak positions in °2θ and d-spacing from a powder XRD pattern of a representative sample of Form B prepared as described herein, yielded unit cell parameters of a=11.609 Å, b=12.341 Å, c=14.674 Å and with a volume=2102.2 Å3.

Applying unit cell refinement (where representative measured peak positions and assigned HKL values are fed into a program which then determined unit cell values for the corresponding crystal structure) yielded the following unit cell parameters using the complete peak list, 6 lowest angle peaks and 5 strongest peaks as listed (with single crystal data provided for comparison):

| Complete Peak List | | | |
|---|---|---|---|
| a = 11.600 Å | b = 12.332 Å | c = 14.659 Å | Vol = 2097.1 Å$^3$ |
| 6 Lowest Angle Peaks @ | | | |
| 9.40 °2θ, 10.54 °2θ, 12.10 °2θ, 14.05 °2θ, 14.35 °2θ and 15.28 °2θ | | | |
| a = 11.572 Å | b = 12.312 Å | c = 14.648 Å | Vol = 2087.0 Å$^3$ |
| 5 Strongest Peaks @ | | | |
| 12.10 °2θ, 15.28 °2θ, 19.51 °2θ, 21.01 °2θ and 24.85 °2θ | | | |
| a = 11.603 Å | b = 12.327 Å | c = 14.632 Å | Vol = 2092.8 Å$^3$ |
| Single Crystal Results | | | |
| a = 11.576 Å | b = 12.336 Å | c = 14.658 Å | Vol = 2093.2 Å$^3$ |

Nalbuphine Crystalline Form A

The single crystal structure of Form A is known. The measured crystal structure is orthorhombic P212121 with unit cell parameters of a=11.729 Å, b=11.533 Å, c=14.408 Å and with a volume=1948.9 Å$^3$. Applying unit cell refinement yielded the following unit cell parameters using the 6 lowest angle peaks, the 5 strongest peaks, shown along with the single crystal unit cell results:

| Single Crystal Results | | | |
|---|---|---|---|
| a = 11.729 Å | b = 11.533 Å | c = 14.408 Å | Vol = 1948.9 Å$^3$ |
| 6 Lowest Angle Peaks @ | | | |
| 9.78 °2θ, 10.77 °2θ, 12.42 °2θ, 14.49 °2θ, 15.06 °2θ and 16.32 °2θ | | | |
| a = 11.746 Å | b = 11.503 Å | c = 14.437 Å | Vol = 1946.8 Å$^3$ |
| 5 Strongest Peaks @ | | | |
| 12.42 °2θ, 14.49 °2θ, 16.32 °2θ, 24.03 °2θ and 25.17 °2θ | | | |
| a = 11.729 Å | b = 11.533 Å | c = 14.408 Å | Vol = 1948.9 Å$^3$ |

Nalbuphine Crystalline Form C

A number of PXRD patterns of Form C were obtained in the solid form screens and this allows some statistical analysis of the observed peak positions and peak separation. The initial unit cell and Miller index allocation was performed based upon the results for Form B. This gives some self consistency between the observed peak and their Miller Indices. That is, peaks that look relatively similar between the measured powder patterns for Forms B and C should have the same Miller Index.

Form C was indexed and refined to the following unit cell: Orthorhombic P212121 with unit cell parameters of a=11.653 Å, b=11.636 Å, c=14.537 Å with volume=1971.0 Å3. With the 'a' and 'b' axes both having very similar lengths, the symmetry of this unit cell can be described as tetragonal. However, the orthorhombic P212121 symmetry is being maintained for self consistency with Form B. For consistency, lattice parameter 'a' is selected as the intermediate length with 'b' being the shortest length. This ensures that the Miller Indices match between Forms A, B, C. The symmetry P212121 gives complete freedom to swap the axes in order or their magnitude.

The primary indexed peaks for Form C were as listed in Table 1, below, where the peak position in °2θ and 'd-spacing' values are associated with a specific Miller Index 'HKL'. The °2θ values were determined from a measured powder XRD pattern and the d-spacing values were derived from these using a mean Cu Kα wavelength of 1.5418 Å. The Miller indices HKL were derived from the indexed and refined unit cell.

TABLE 1

Key Peaks for Form C with Miller Index HKL

| PXRD Data | | Miller Indices | | |
|---|---|---|---|---|
| °2θ | d-value Å | H | K | L |
| 9.76 | 9.062 | 0 | 1 | 1 |
| 10.75 | 8.230 | 1 | 1 | 0 |
| 12.37 | 7.155 | 1 | 1 | 1 |
| 14.35 | 6.172 | 0 | 1 | 2 |
| 15.22 | 5.821 | 2 | 0 | 0 |
| 16.27 | 5.448 | 1 | 1 | 2 |
| 16.99 | 5.219 | 1 | 2 | 0 |
| 18.07 | 4.909 | 2 | 1 | 1 |
| 19.51 | 4.550 | 0 | 2 | 2 |
| 21.25 | 4.181 | 1 | 1 | 3 |
| 22.42 | 3.965 | 2 | 2 | 1 |
| 24.19 | 3.679 | 3 | 1 | 0 |
| 25.09 | 3.549 | 2 | 1 | 3 |
| 25.69 | 3.468 | 0 | 1 | 4 |
| 27.13 | 3.287 | 1 | 3 | 2 |
| 27.58 | 3.234 | 2 | 3 | 0 |

Applying unit cell refinement yielded the following unit cell parameters using the 6 lowest angle peaks, the 5 strongest peaks, and the best indexing results:

| Best Indexing Results | | | |
|---|---|---|---|
| a = 11.653 Å | b = 11.636 Å | c = 14.537 Å | Vol = 1971.0 Å$^3$ |
| 6 Lowest Angle Peaks @ | | | |
| 9.76 °2θ, 10.75 °2θ, 12.37 °2θ, 14.35 °2θ, 15.22 °2θ and 16.27 °2θ | | | |
| a = 11.644 Å | b = 11.603 Å | c = 14.551 Å | Vol = 1967.4 Å$^3$ |
| 5 Strongest Peaks @ | | | |
| 12.37 °2θ, 14.35 °2θ, 16.27 °2θ, 19.51 °2θ and 21.25 °2θ | | | |
| a = 11.584 Å | b = 11.651 Å | c = 14.565 Å | Vol = 1965.9 Å$^3$ |

The Miller Index values for Forms A and C are very similar, reflecting the close similarity of the two crystal structures. Specificity was enhanced between Forms A and C using unit cell refinement. The data listed above demonstrates that specificity can easily be achieved between Forms A and C using unit cell refinement provided that 5 or 6 diffraction peaks specific to each form can be identified in the measure data.

PXRD Peak Pairs

For Forms A and C, where single crystal data was measured and self consistent indexing was performed, the tables of peaks can be reduced to a series of peak pairs. The selected peak pairs represent the most characteristic peaks for each form (either the most intense or stand alone at low angles) and are listed in Table 2, below.

TABLE 2

Miller Indicies (HKL) & Peak Positions, Form A and Form C

| Peak Positions °2θ | | Miller Indices | | |
|---|---|---|---|---|
| Form A | Form C | H | K | L |
| 9.78 | 9.76 | 0 | 1 | 1 |
| 10.77 | 10.75 | 1 | 1 | 0 |
| 12.42 | 12.37 | 1 | 1 | 1 |
| 14.49 * | 14.35 * | 0 | 1 | 2 |
| 15.06 * | 15.22 * | 2 | 0 | 0 |
| 16.32 | 16.27 | 1 | 1 | 2 |
| 17.10 | 16.99 | 1 | 2 | 0 |
| 18.03 | 18.07 | 2 | 1 | 1 |
| 19.71 ** | 19.51 ** | 0 | 2 | 2 |
| 21.42 * | 21.25 * | 1 | 1 | 3 |
| 22.47 | 22.42 | 2 | 2 | 1 |
| 24.03 * | 24.19 * | 3 | 1 | 0 |
| 25.17 | 25.09 | 2 | 1 | 3 |
| 25.89 ** | 25.69 ** | 0 | 1 | 4 |
| 27.42 ** | 27.13 ** | 1 | 3 | 2 |
| 27.75 * | 27.58 * | 2 | 3 | 0 |

Peak positions marked with ** have positions that different by 0.2 °2θ or greater while those marked * have positions that differ by 0.1 °2θ or more.

Comparing Form C and Form A, of the characteristic peak list only 3 peaks differ in their measured positions by ±0.2°2θ or more. An additional 5 peaks differ in their measured positions by ±0.1°2θ or more.

Due to their similarity, Forms A and C have the same peak families and the same robust peak pair relationships. However, due to the reduced error associated with peak separation measurements some of the characteristic peak pairs may be specific, as listed in Table 3 below. Forms A and C represent similar structures with a slight difference in water content. The shift in unit cell volume between the two forms is close to the volume required for a single water molecule. This corresponds to a change in composition of approximately ¼ molecule of water per molecule of compound. Even with this very subtle difference in structure, some of the most characteristic HKL pair distances are specific to one form over the other. If the pair separation distance is given an error of ~0.1°2θ, then 4 of the pair distances are specific. If this error window is dropped to 0.05°2θ, then 6 of the pair distances are specific for either form.

TABLE 3

Robust Peak Pairs & Peak Separation, Form A & Form C

| HKL pair | Family | Form A (°2θ) | Form C (°2θ) | Δ (HKL pair) between Form A and Form C |
|---|---|---|---|---|
| (011)-(022) ** | Y | 9.93 | 9.75 | 0.18 |
| (110)-(111) | N | 1.65 | 1.62 | 0.03 |
| (111)-(211) * | N | 5.61 | 5.70 | 0.09 |
| (012)-(112) * | N | 1.83 | 1.92 | 0.09 |
| (110)-(310) ** | N | 13.26 | 13.44 | 0.18 |
| (111)-(113) ** | N | 9.00 | 8.88 | 0.12 |
| (011)-(014) ** | N | 16.11 | 15.93 | 0.18 |

HKL Pairs marked with ** are potentially specific to Form A or Form C with an error window ~0.1. HKL Pairs marked with * are potentially specific to Form A or Form C with an error window of ~0.05

Some of the forms of nalbuphine HCl as herein described were additionally analyzed by to one or more of the following techniques, with measurement and analysis conditions applied as described below.

Differential Scanning Calorimetry (DSC)

Differential scanning calorimetry (DSC) was performed using a TA Instruments differential scanning calorimeter 2920. The sample was placed into an aluminum DSC pan, and the weight accurately recorded. The pan was covered with a lid and sometimes crimped. The sample cell was generally equilibrated at ambient temperature and heated under a nitrogen purge at a rate of 10° C./min, up to a final temperature of 250° C. or 350° C., as noted. One sample was analyzed from −50° C. to 350° C. Indium metal was used as the calibration standard. Reported temperatures are at the transition maxima.

Differential scanning calorimetry (DSC) was performed on representative samples of nalbuphine HCl Form A, Form B, Form C, Form D, Form F, Form G, Form H, Form I, Form K and Form U, with results as described hereinafter.

Thermogravimetric Analysis (TGA)

Thermogravimetric analysis (TGA) was performed using a TA Instruments 2950 thermogravimetric analyzer. The sample was placed in an aluminum sample pan and inserted into the TG furnace. The furnace was first equilibrated at 25° C., then heated under nitrogen at a rate of 10° C./min, up to a final temperature of 150° C., 215° C. or 350° C., as noted. Nickel and Alumel™ were used as the calibration standards. The samples heated to 150° C. and 215° C. were recovered for PXRD analysis.

Thermogravimetric analysis (TGA) was performed on representative samples of nalbuphine HCl Form A, Form F, Form I, Form K and Form U, with results are described hereinafter.

Karl-Fischer Titration (% Water Content)

Coulometric Karl Fischer (KF) analysis for water determination was performed using a Mettler Toledo DL39 Karl Fischer titrator. Approximately 10-33 mg of sample was placed in the KF titration vessel containing Hydranal—Coulomat AD and mixed for 10 seconds to ensure dissolution. The sample was then titrated by means of a generator electrode which produces iodine by electrochemical oxidation: 2 I−≧I$_2$+2e. Three replicates were obtained to ensure reproducibility. The mean value of the replicates is reported herein.

Karl-Fischer measurements were performed on representative samples of nalbuphine HCl Form B, Form C, Form D and Form G, with results as described hereinafter.

Automated Moisture Sorption/Desorption Analysis

Moisture sorption/desorption data were collected on a VTI SGA-100 Vapor Sorption Analyzer. Sorption and desorption data were collected over a range of 5% to 95% relative humidity (RH) at 10% RH intervals under a nitrogen purge. Samples were not dried prior to analysis. Equilibrium criteria used for analysis were less than 0.0100% weight change in 5 minutes with a maximum equilibration time of 3 hours if the weight criterion was not met. Data were not corrected for the initial moisture content of the samples and reported values are with respect to the initial sample mass. Sodium chloride and polyvinylpyrrolidone were used as calibration standards. A sample was taken after desorption was complete and analyzed by powder X-ray diffraction for potential form change.

Automated moisture sorption/desorption data was collected for representative samples of nalbuphine HCl Form A, Form B, Form C, Form D and Form E, as shown in FIG. 12, FIG. 13, FIG. 14, FIG. 15 and FIG. 16, respectively.

Hot Stage Microscopy

Hot stage microscopy was performed using a Linkam hot stage (model FTIR 600) mounted on a Leica DM LP. The sample was observed using a 20× objective with crossed polarizers and a first order red transition plate. The sample was mounted between two coverslips (without oil) and was visually observed as the stage was heated. Crystalline Forms A, C and G were analyzed by hot stage microscopy with results as described hereinafter.

The following are summaries of the physical properties of nalbuphine HCl crystalline Forms A, B, C, D, F, G, H, I, K and U, and amorphous Form Z, based on the measurements and analyses completed as described herein.

Nalbuphine HCl Crystalline Form A

Figure 17:
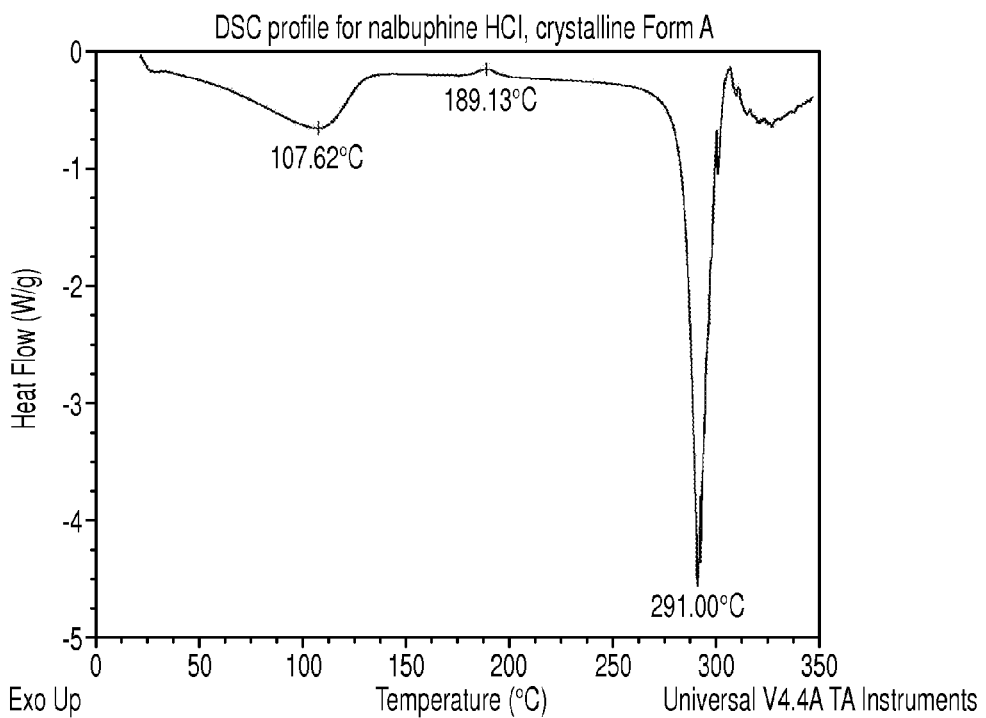
FIG. 17 illustrates a Differential Scanning calorimetry (DSC) profile for nalbuphine HCl crystalline Form A.

Nalbuphine HCl form A is the commercially produced form. Form A is a hemihydrate with Karl-Fisher water titration showing 2.41% of water in the sample, corresponding to 0.5 mole of water per mole of nalbuphine HCl. Upon heating, Form A converts to Form F, at about 190° C. before melting near 290° C. The TGA (thermogravimetric analysis) data showed a weight loss of 4.3% between 22° C. and 140° C., equating to approximately 1 mole of water. The DSC (as shown in FIG. 17) showed a broad endotherm at 108° C. corresponding to the water loss, a small exotherm at 189° C., corresponding to a recrystallization as confirmed by hot stage microscopy, followed by a sharp endotherm at 291° C., a melting event.

Form A converts to Form C (monohydrate) when exposed to elevated relative humidity such as 50% RH or above, and to Form B (dihydrate) at extremely high humidity such as 97% RH. Form A is physically unstable when large amounts of mechanical stress are applied, converting to Form C (under compression or dry grinding), or Form B (under wet grinding). Further grinding caused some loss of crystallinity and formed partially amorphous material as evident from X-ray powder diffraction analysis.

By hot stage microscopy, birefringent prisms was visible by approximately 201° C. and recrystallization was complete by approximately 207° C. No further change was observed in crystalline Form A, even upon cooling.

Nalbuphine HCl Form B

Figure 18:
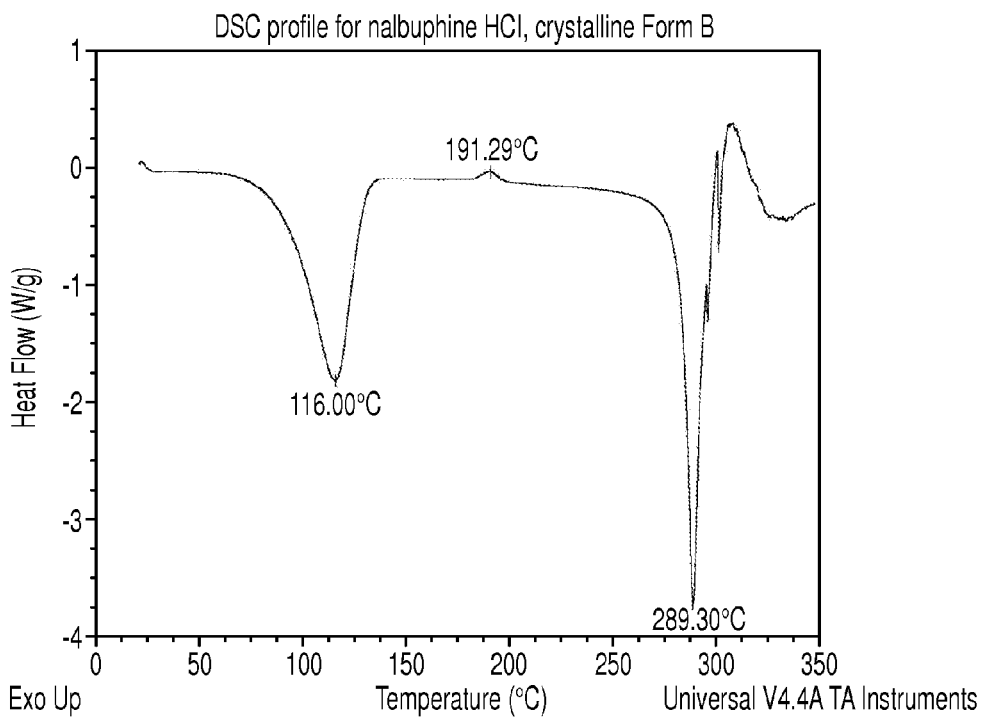
FIG. 18 illustrates a Differential Scanning calorimetry (DSC) profile for nalbuphine HCl crystalline Form B.

Nalbuphine HCl form B is a dihydrate and its single crystal structure is known in the literature (R. J. Sime, M. Dobler, R. L. Sime *Acta Crystallogr*, B: *Struct. Crystallogr. Cryst. Chem.*, 1976, 32, 809). Karl Fisher water titration on Form B showed 9.29% of water in the sample, corresponding to about 2 moles of water per mole of nalbuphine HCl. The DSC (shown in FIG. 18) exhibited a broad endotherm at 116° C. (water loss), followed by an exotherm at 191° C. (recrystallization) and a sharp endotherm at 289° C. (melt). Upon heating, Form B converts to Form F at about 190° C. before melting near 290° C.

Form B is physically unstable when milled, losing its crystallinity as evident from X-ray powder diffraction analysis. Form B was physically unstable when dried at 60° C., mostly converting to Form C (monohydrate).

Nalbuphine HCl Form C

Figure 19:
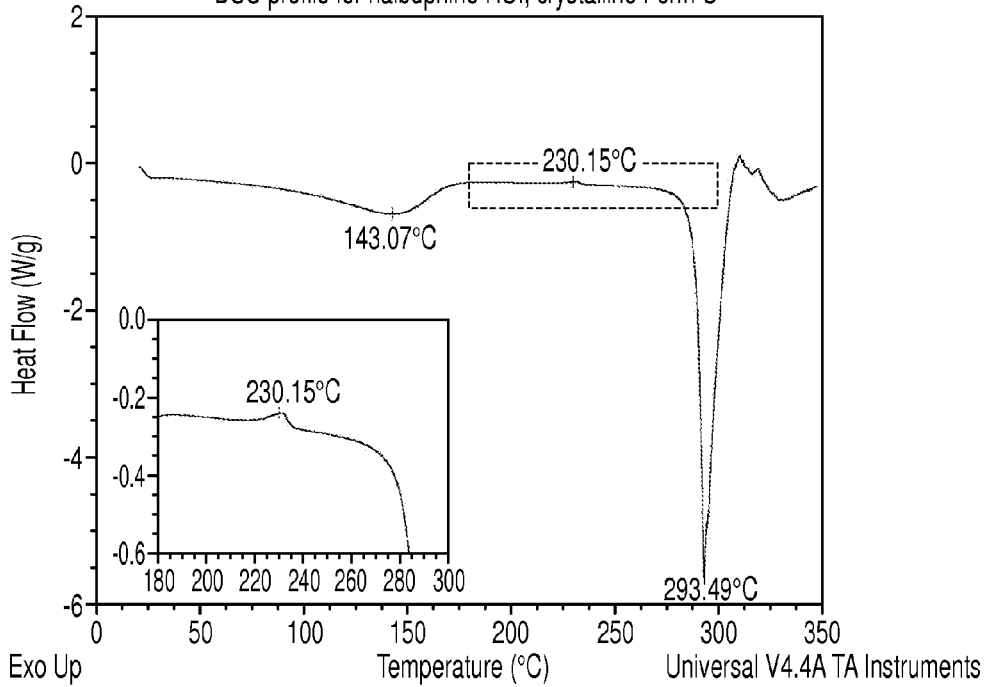
FIG. 19 illustrates a Differential Scanning calorimetry (DSC) profile for nalbuphine HCl crystalline Form C.

Nalbuphine HCl form C is a stable monohydrate, with Karl Fisher water titration showing 3.92% of water in the sample, corresponding to about 1 mole of water per mole of nalbuphine HCl. Upon heating, Form C converts to Form F at 200° C., before melting near about 290° C. The DSC (shown in FIG. 19) exhibits a broad endotherm at 143° C. (water loss), followed by a sharp endotherm at 293° C. which corresponds to a melt as confirmed by hot stage microscopy analysis. There is also a small exothermic event at approximately 232° C. in the DSC data and this was confirmed to be recrystallization to Form F by VT-XRPD analysis.

Form C can be prepared from known Form A by mixing in solvents with excess solids for about a week at either ambient or elevated temperatures, drying the recovered solids under high relative humidity (such as 60% RH). Form C can also be prepared by evaporating a solution of Form A in methanol/butanone, or methanol/p-dioxane, or methanol/ethyl acetate, or methanol/methyl isobutyl ketone, under high relative humidity (such as 48% RH). At extreme high humidity conditions such as 97% RH, Form C converts to Form B (dihydrate).

By hot stage microscopy, Form C exhibited a partial change in birefringence at 150° C., but no further change by 190° C. Form C further exhibited recrystallization onset at about 214° C., recrystallization completion by about 219° C. and a slight change in appearance upon cooling.

Nalbuphine HCl Form D

Figure 20:
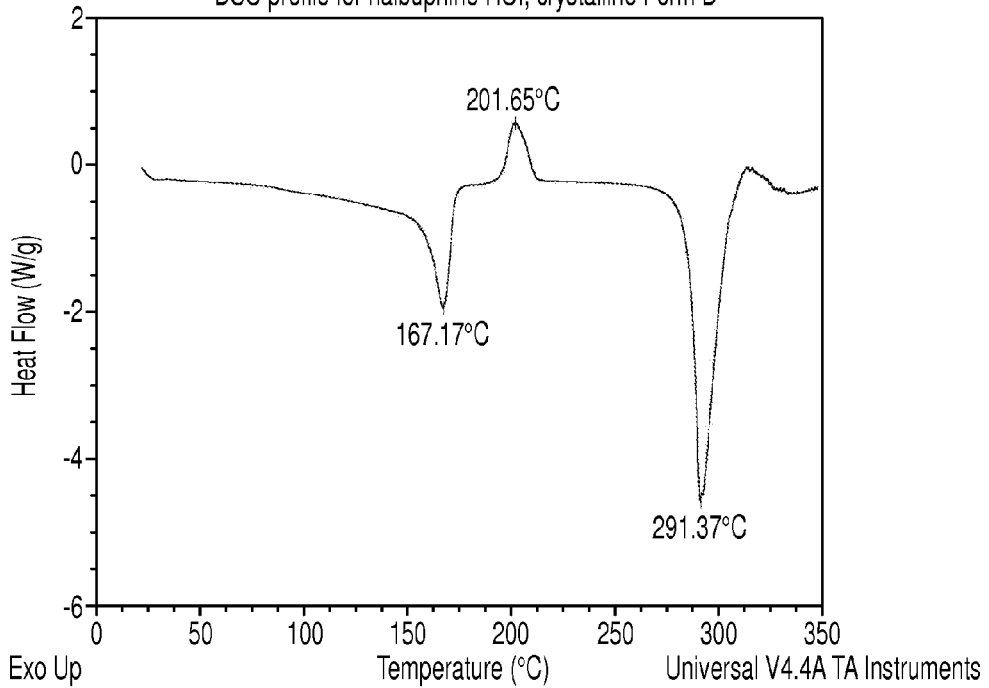
FIG. 20 illustrates a Differential Scanning calorimetry (DSC) profile for nalbuphine HCl crystalline Form D.

Nalbuphine HCl form D is a stable sesquihydrate form, with Karl Fisher water titration showing 7.53% of water in the sample, corresponding to about 1.5 moles of water per mole of nalbuphine HCl. The DSC (shown in FIG. 20) exhibited an endotherm at 167° C. (loss of water), followed by an exotherm at 202° C. (recrystallization) and a sharp endotherm at 291° C. (melt).

Form D may be prepared from slow evaporation of clear solution containing nalbuphine HCl Form A in one of the following solvent systems at relative humidity of approximately 48% to 52% RH: methanol/nitromethane, methanol/acetonitrile, water/acetonitrile, water/p-dioxane, ethanol, 2-propanol, methanol. Form D was also prepared from slow evaporation of a clear solution containing nalbuphine HCl Form A in one of the following solvent systems at relative humidity of approximately 44% to 52% RH: 2,2,2-trifluoroethanol, or hexafluoroisopropanol. At extreme high humidity conditions such as 97% RH, Form D converts to Form B (dihydrate). Upon heating, Form D converts to Form F at about 180° C. before melting near 290° C.

Nalbuphine HCl Form F

Figure 21:
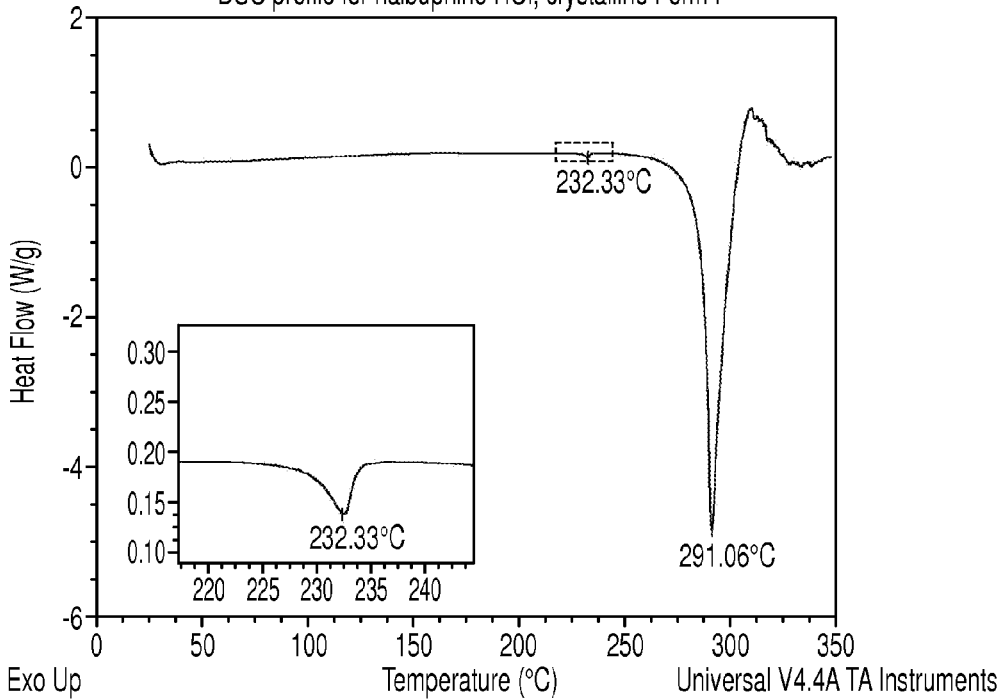
FIG. 21 illustrates a Differential Scanning calorimetry (DSC) profile for nalbuphine HCl crystalline Form F.

Nalbuphine HCl form F is a stable anhydrate. The TGA data of Form F showed weight loss of 0.02% up to 191° C., confirming the material is anhydrous. The DSC (shown in FIG. 21) showed a small endotherm at 232° C., followed by a sharp endotherm at 291° C. which is the melt of Form F. This is supported by VT-XRPD, for which Form F was observed when other crystalline forms were heated at temperatures between 180° C. and 220° C.

Form F may be prepared by heating other crystalline forms, such as Form A or Form B above, to approximately 180-190° C. Form F may further be obtained through elevated temperature (about 50° C.) slurry (for about seven days) in tetrahydrofuran, yielding a mixture containing Form F as the major component with a small amount of Form C. At extremely high humidity conditions such as 85% RH, Form F converts to Form B (dihydrate). Upon heating, Form F melts near 290° C.

Nalbuphine HCl Form G

Figure 22:
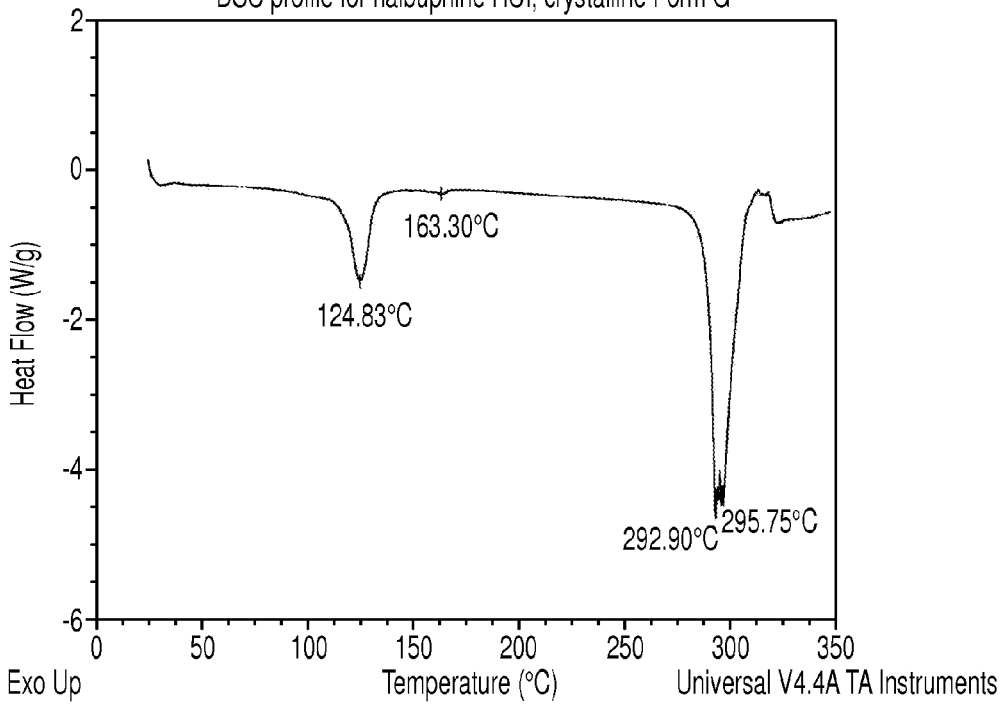
FIG. 22 illustrates a Differential Scanning calorimetry (DSC) profile for nalbuphine HCl crystalline Form G.

Nalbuphine HCl Form G is a monohydrate, with Karl Fisher water titration showing 4.08% of water in the sample, corresponding to about 1 mole of water per mole of nalbuphine HCl. The DSC (shown in FIG. 22) showed an endotherm at 125° C. (water loss), followed by a shallow endotherm at 163° C. (water loss) and a sharp endotherm with maxima at 293-296° C. (melt). By hot stage microscopy, the material exhibited a partial change in birefringence at 150° C., recrystallization onset at approximately 191° C., visible birefringent prisms by approximately 201° C., recrystallization completion by approximately 218° C., and no change upon cooling.

Form G may be prepared by precipitation from solutions in methanol by adding anti-solvent acetonitrile.

By hot stage microscopy, Form G exhibited a partial change in birefringence at 150° C., recrystallization onset at about 191° C., visible birefringent prisms by about 201° C., recrystallization completion by about 218° C., and no change upon cooling.

Nalbuphine HCl Form H

Nalbuphine HCl Form H is a monohydrate/monomethanolate. The DSC (based on an analysis of a mixture of Form H and Form C and a second mixture of Form H and Form I) showed an endotherm at 88° C., followed by a broad endotherm at 132° C., a shallow endotherm at 157° C., a shallow exotherm at 192° C. (recrystallization), and a sharp endotherm with maxima at 292-295° C. (melt).

The structure identity was obtained by single crystal X-ray diffraction structure solution at 150 Kelvin. The triclinic cell parameters and calculated volume are: a=8.2547(7) Å, b=8.5527(6) Å, c=8.9454(5) Å, $\alpha$ 110.146(3) °, $\beta$=112.487(3) °, $\gamma$=93.264(2) °, V=534.71(7) Å$^3$. The formula weight for the contents of the asymmetric unit for Nalbuphine HCl Form H is 443.97 g mol$^{-1}$ with Z=1 resulting in a calculated density of 1.379 g cm$^{-3}$. The space group was determined to be P 1 (No. 1).

Form H may be prepared by precipitation from solutions in methanol by adding anti-solvent ethyl acetate.

Nalbuphine HCl Form I

Figure 23:
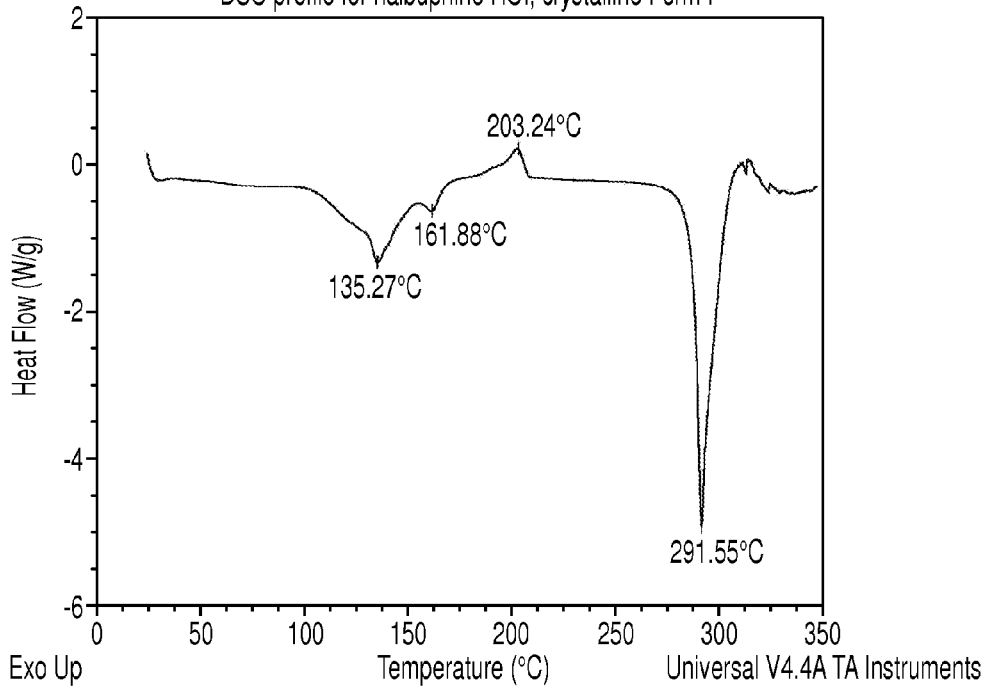
FIG. 23 illustrates a Differential Scanning calorimetry (DSC) profile for nalbuphine HCl crystalline Form I.

Nalbuphine HCl Form I is a monomethanolate. TGA data showed weight loss of 8.0% up to 113° C., corresponding to 1.1 moles of methanol. The proton NMR spectrum of Form I confirmed methanol present in the sample. The DSC (shown in FIG. 23) showed a broad endotherm at 135° C. (loss of methanol), followed by an endotherm at 162° C., an exotherm at 203° C. (recrystallization) and a sharp endotherm at 292° C. (melt).

Form I may be prepared by evaporation from solutions in methanol at low controlled relative humidity such as 17% RH.

Nalbuphine HCl Form K

Figure 24:
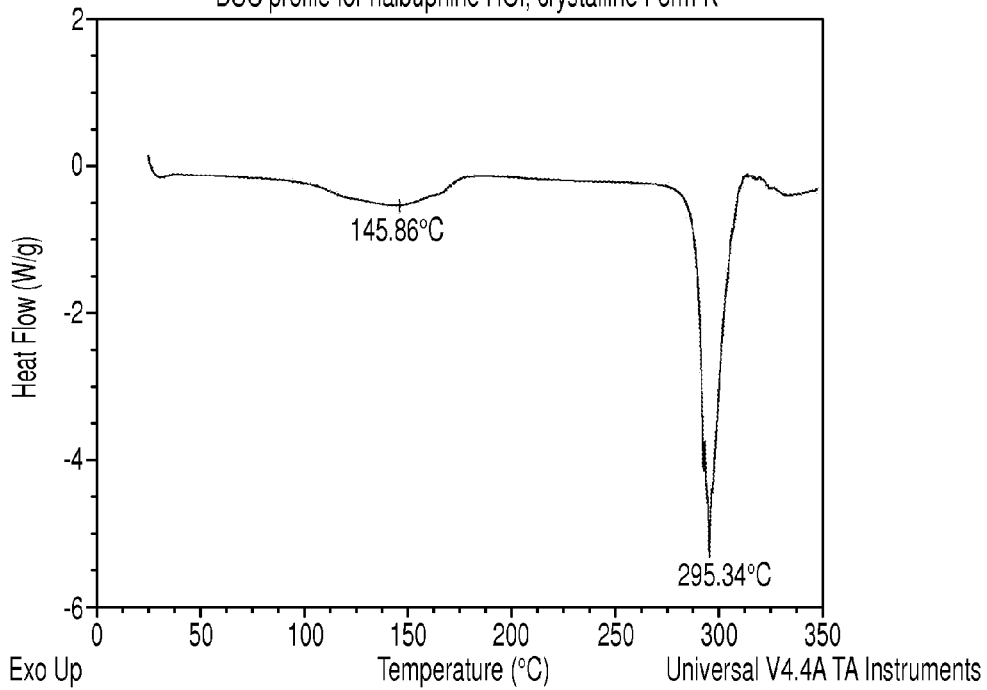
FIG. 24 illustrates a Differential Scanning calorimetry (DSC) profile for nalbuphine HCl crystalline Form K.

Nalbuphine HCl Form K is a monohydrate, with TGA showing 4.46% of water in the sample which corresponds to about 1 mole of water per mole of nalbuphine HCl. The DSC (shown in FIG. 24) showed a broad endotherm at 146° C. (loss of water), followed by an endotherm at 295° C. (melt).

Form K may be prepared by evaporation from solutions in ethanol at low controlled relative humidity such as 17% RH.

Nalbuphine HCl Form U

Figure 25:
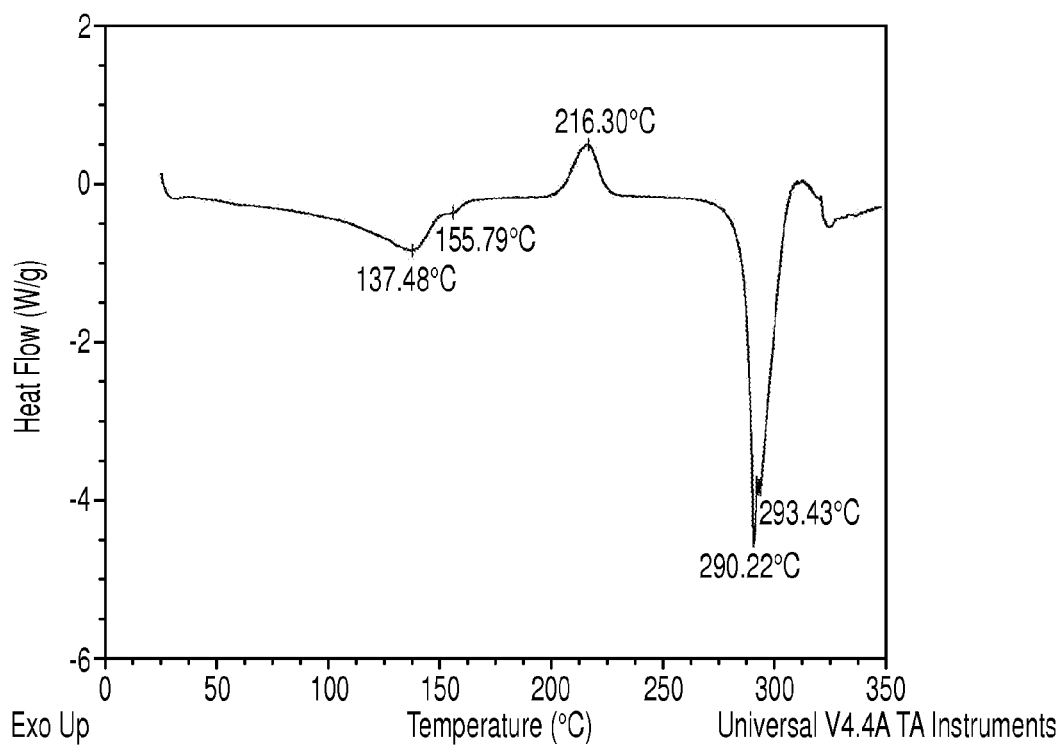
FIG. 25 illustrates a Differential Scanning calorimetry (DSC) profile for nalbuphine HCl crystalline Form U.

Nalbuphine HCl Form U is a sesquihyhydrate, with TGA showing 6.33% of water in the sample, corresponding to about 1.5 moles of water per mole of nalbuphine HCl. The DSC (shown in FIG. 25) showed an endotherm at 137° C. (loss of water), followed by a shallow endotherm at 156° C., an exotherm at 216° C. (recrystallization) and a sharp endotherm with maxima at 290-293° C. (melt).

Form U may be prepared by freeze drying solutions in tert-butanol/water.

Nalbuphine HCl Amorphous Form Z

The nalbuphine HCl amorphous form exhibits a glass transition temperature of 48° C. Amorphous Form Z may be prepared by evaporating a clear solution of Form A, prepared using one of the following solvents at low relative humidity such as 17% RH: 2,2,2-trifluoroethanol, 2-propanol, 1-propanol.

Pharmaceutical Compositions

The present invention also provides pharmaceutical compositions comprising one or more of the nalbuphine HCl crystalline and/or amorphous forms as herein described in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of providing an analgesic effect described in the present invention may also be carried out using a pharmaceutical composition comprising any of the compounds as defined herein and a pharmaceutically acceptable carrier. The pharmaceutical composition may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms may include suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

To prepare a pharmaceutical composition of the present invention, a compound of formula (I) as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

The nalbuphine HCl crystalline and/or amorphous forms as herein described may be administered in any of the foregoing compositions and according to dosage regimens established in the art whenever analgesia is required.

The daily dosage of the products may be varied over a wide range from 0.01 mg to about 1,000 mg per adult human per day, or any amount or range therein, preferably from about 5 mg to about 50 mg per adult human per day, or any amount or range therein. For oral administration, the compositions are preferably provided in the form of tablets containing about, 0.01, 0.05, 0.1, 0.5, 1.0, 2.5, 5.0, 7.5, 10, 25, 50, 100, 150, 250, 300, 400, 500 and 1000 milligrams of the active ingredient for the symptomatic adjustment of the dosage to the patient to be treated. An effective amount of the drug is ordinarily supplied at a dosage level of from about 0.01 mg/kg to about 15 mg/kg of body weight per day, or any amount range therein. Preferably, the range is from about 0.05 to about 10 mg/kg of body weight per day, or any amount or range therein. Preferably, the range is from about 0.1 to about 7 mg/kg of body weight per day, or any amount or range therein. Preferably, the range is from about 1 to about 5 mg/kg of body weight per day, or any amount or range therein. The compounds may be administered on a regimen of 1 to 4 times per day.

Optimal dosages and dosage regimens to be administered may be readily determined by those skilled in the art, and will vary with the mode of administration, the strength of the preparation and the advancement of the disease condition. In addition, factors associated with the particular patient being treated, including patient's sex, age, weight, diet, physical activity, time of administration and concomitant diseases, will result in the need to adjust dosages and/or regimens.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy patients and/or those suffering from a given disorder, may be completed according to methods well known in the clinical and medical arts.

EXAMPLES

The following Examples are set forth to aid in the understanding of the invention, and are not intended and should not be construed to limit in any way the invention set forth in the claims which follow thereafter. Unless otherwise noted, all solvents used were either HPLC grade or ACS reagent grade.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Unless otherwise noted, nalbuphine HCl, Form A was used as the starting material in the Examples which follow herein.

Example 1

Preparation of Nalbuphine HCl Form A

Nalbuphine HCl, Form A (~29 mg) was completely dissolved in water (2 mL) with the aid of ultrasonication. The solution was allowed to evaporate to dryness in an open vial under nitrogen atmosphere (approximate relative humidity 17% RH) at ambient temperature to yield Form A.

Example 2

Preparation of Nalbuphine HCl Form a

Nalbuphine HCl, Form A (~42 mg) was completely dissolved in acetone and water (1:1 v/v; 0.2 mL) with the aid of ultrasonication. The solution was allowed to evaporate to dryness in an open vial under nitrogen atmosphere (approximate relative humidity 17% RH) at ambient temperature to yield Form A.

Example 3

Preparation of Nalbuphine HCl Form B

Nalbuphine HCl, Form A (~38 mg) was completely dissolved in water (1.1 mL). The solution was filtered via 0.2 micron nylon filter and allowed to evaporate to dryness in an open vial in a laboratory hood (52% RH) and at ambient temperature to yield Form B.

Example 4

Preparation of Nalbuphine HCl Form B

Nalbuphine HCl, Form A (~40 mg) was completely dissolved in acetone and water (16:4 v/v; 0.8 mL). The solution was filtered via 0.2 micron nylon filter and allowed to evaporate to dryness in an open vial in a laboratory hood (52% RH) and at ambient temperature to provide the title form.

In a separate example, crystalline form B was also obtained following the above described procedure, substituting acetone and water (1:1 v/v) for the solvent system.

Example 5

Preparation of Nalbuphine HCl Form B

Nalbuphine HCl, Form A (~40 mg) was completely dissolved in acetonitrile and water (16:4 v/v; 1.7 mL). The solution was filtered via 0.2 micron nylon filter and allowed to evaporate to dryness in an open vial in a laboratory hood (52% RH) and at ambient temperature to yield Form B.

Example 6

Preparation of Nalbuphine HCl Form B

Nalbuphine HCl, Form A (~39 mg) was completely dissolved in 2-propanol and water (17:3 v/v; 3.5 mL). The solution was filtered via 0.2 micron nylon filter and allowed to evaporate to dryness in an open vial in a laboratory hood (52% RH) and at ambient temperature to yield Form B.

Example 7

Preparation of Nalbuphine HCl Form B

Nalbuphine HCl, Form A (~105 mg) was completely dissolved in 1-propanol and water (17:3 v/v; 7 mL) at 50° C. The solution was hot filtered via 0.2 micron nylon filter and a portion of the solution (3.5 mL) was placed in a freezer (−22° C.) for 17 days. A white solid formed and was recovered by decanting off the supernatant, then dried in nitrogen atmosphere (17% RH) for about 1.5 hours to yield Form B.

Example 8

Preparation of Nalbuphine HCl Form B

Nalbuphine HCl, Form A (~105 mg) was completely dissolved in 1-propanol and water (17:3 v/v; 7 mL) at 50° C. The solution was hot filtered via 0.2 micron nylon filter and a portion of the solution (3.5 mL) in a capped vial was allowed to cool to ambient temperature for one day. The resulting clear solution was then placed in a refrigerator (6° C.) for one day. The clear solution was further cooled in a freezer (−22° C.) for 15 days. A white solid formed and was recovered by decanting off the supernatant, then dried in nitrogen atmosphere (17% RH) for about 1.5 hours to yield Form B.

Example 9

Preparation of Nalbuphine HCl Form B

Nalbuphine HCl, Form A (~38 mg) was completely dissolved in 1-butanol (11 mL). The solution was filtered via 0.2 micron nylon filter and allowed to evaporate to dryness in an open vial in a laboratory hood (52% RH) and at ambient temperature to yield Form B.

Example 10

Preparation of Nalbuphine HCl Form B

Nalbuphine HCl, Form A (~39 mg) was completely dissolved in ethanol (3 mL). The solution was filtered via 0.2 micron nylon filter and allowed to evaporate to dryness in an open vial in a laboratory hood (52% RH), then at ambient temperature to yield Form B.

Following the above described procedure Form B was also obtained when substituting 2-propanol for ethanol.

Example 11

Preparation of Nalbuphine HCl Form B

Nalbuphine HCl, Form A (~311 mg) was completely dissolved in methanol (3 mL) and the solution filtered via 0.2 micron nylon filter. An aliquot of the solution (0.5 mL) was mixed with toluene (2 mL) and the resulting clear solution was allowed to evaporate to dryness in a vial covered with perforated aluminum foil in a laboratory hood (48% RH) and at ambient temperature to yield Form B.

Example 12

Preparation of Nalbuphine HCl Form B

Nalbuphine HCl, Form A (~106 mg) was completely dissolved in water (3 mL) and filtered via 0.2 micron nylon filter. An aliquot of the solution (1 mL) was mixed with tetrahydrofuran (5 mL) and the resulting clear solution was allowed to evaporate to dryness in a vial covered with perforated aluminum foil in a laboratory hood (48% RH) and ambient temperature to yield Form B.

Example 13

Preparation of Nalbuphine HCl Form B

Nalbuphine HCl, Form A (~250 mg) was completely dissolved in methanol (1 mL) and filtered via 0.2 micron nylon filter. An aliquot of the solution (0.2 mL) was mixed with dichloromethane (5 mL) and the resulting precipitates were vacuum filtered and air dried for approximately 2 minutes to yield Form B.

Example 14

Preparation of Nalbuphine HCl Form B

Nalbuphine HCl, Form A (~205 mg) was completely dissolved in methanol (0.75 mL) with an aid of ultrosonication and filtered via 0.2 micron nylon filter. An aliquot of the solution (0.15 mL) was mixed with nitromethane (9 mL), and precipitates were formed in the solution. The sample was allowed to stand overnight. The solids were recovered by decanting the solvent then air dried using compressed air to yield Form B.

Example 15

Preparation of Nalbuphine HCl Form B

Nalbuphine HCl, Form A (200 mg) was completely dissolved in methanol (0.6 mL) and filtered via 0.2 micron nylon filter. Acetonitrile (20 mL) was added with stirring and the resulting precipitates were vacuum filtered and air dried for approximately 5 minutes to yield Form B.

Following the procedure described above, substituting ethyl acetate, or tetrahydrofuran for acetonitrile also yielded Form B.

Example 16

Preparation of Nalbuphine HCl Form B

Nalbuphine HCl, Form A (~205 mg) was completely dissolved in methanol (0.75 mL) with an aid of ultra-sonication and filtered via 0.2 micron nylon filter. An aliquot of the solution (0.15 mL) was mixed with toluene (14 mL), and the resulting hazy suspension was allowed to stand overnight, then placed in a refrigerator (6° C.) overnight. The hazy suspension was further cooled in a freezer (−13° C.) for four days. The solids were recovered by vacuum filtration to yield Form B.

Example 17

Preparation of Nalbuphine HCl Form C

A sample of nalbuphine HCl Form A was placed under dynamic vapor sorption conditions from 5% to 95% RH, then desorption conditions from 95% to 5% RH at 25° C. to yield Form C.

Example 18

Preparation of Nalbuphine HCl Form C

Solid samples of nalbuphine HCl Form A were placed in the following solvents/temperature, and the resulting slurry samples (solids present in the solvent) were continuously mixed in an orbit shaker for approximately one week. All solvents used were HPLC grade. The solids remaining were recovered by decanting the solvents and air dried in a laboratory hood (60% RH), to yield Form C:

| Listing of Solvent/Temperature Conditions That Yield Form C | | |
| --- | --- | --- |
| acetone/ambient | acetone/50° C. | acetonitrile/ambient |
| acetonitrile/50° C. | 1-butanol/ambient | 1-butanol/50° C. |
| 2-butanone/ambient | 2-butanone/50° C. | dichloromethane/ambient |
| p-dioxane/ambient | p-dioxane/50° C. | ethyl acetate/ambient |
| ethyl acetate/50° C. | heptane/ambient | heptane/50° C. |
| 1-propanol/ambient | 1-propanol/50° C. | tetrahydrofuran/ambient |
| toluene/ambient | toluene/50° C. | 2-propanol/ambient |
| 2-propanol/50° C. | isopropyl ether/ambient | methyl tert-butyl ether/ambient |
| methyl isobutyl ketone/ambient | methyl isobutyl ketone/50° C. | nitromethane/ambient |
| nitromethane/50° C. | | |

Example 19

Preparation of Nalbuphine HCl Form C

Nalbuphine HCl Form A (~311 mg) was completely dissolved in methanol (3 mL) and the solution filtered via 0.2 micron nylon filter. An aliquot of the solution (0.5 mL) was mixed with 2-butanone (2 mL) and the resulting clear solution was allowed to evaporate to dryness in a vial covered with perforated aluminum foil in a laboratory hood (48% RH) and at ambient temperature to yield Form C.

Following the above procedure, substituting p-dioxane, ethyl acetate, or methyl isobutyl ketone for 2-butanone also yielded Form C.

Example 20

Preparation of Nalbuphine HCl Form D

Nalbuphine HCl, Form A (~311 mg) was completely dissolved in methanol (3 mL) and the solution filtered via 0.2 micron nylon filter. An aliquot of the solution (0.5 mL) was mixed with nitromethane (2 mL) and the resulting clear solution was allowed to evaporate to dryness in a vial covered with perforated aluminum foil in a laboratory hood (48% RH) and at ambient temperature to yield Form D.

Following the above procedure, substituting acetonitrile for nitromethane also yielded Form D.

Example 21

Preparation of Nalbuphine HCl Form D

Nalbuphine HCl, Form A (~106 mg) was completely dissolved in water (3 mL) and filtered via 0.2 micron nylon filter. An aliquot of the solution (1 mL) was mixed with acetonitrile (5 mL) and the resulting clear solution was allowed to evaporate to dryness in a vial covered with perforated aluminum foil in a laboratory hood (48% RH) and ambient temperature to yield Form D.

Following the above procedure, substituting p-dioxane for acetonitrile also yielded Form D.

Example 22

Preparation of Nalbuphine HCl Form D

Nalbuphine HCl, Form A (~519 mg) was completely dissolved in ethanol (4 mL) and filtered via 0.2 micron nylon filter. The clear solution was allowed to evaporate to dryness in a vial covered with perforated aluminum foil in a laboratory hood (52% RH) and ambient temperature to yield Form D.

Following the above procedure, substituting 2-propanol (429 mg/7 mL) or methanol (514 mg/2 mL) for ethanol also yielded Form D.

Example 23

Preparation of Nalbuphine HCl Form D

Nalbuphine HCl, Form A (~40 mg) was completely dissolved in 2,2,2-trifluoroethanol (0.2 mL). Additional 2,2,2-trifluoroethanol (0.8 mL) was added to aid filtration, the resulting mixture filtered via 0.2 micron nylon filter. The solution was then allowed to evaporate to dryness in an open vial in a laboratory hood (approximate relative humidity 52% RH) at ambient temperature to yield Form D.

Example 24

Preparation of Nalbuphine HCl Form D

Nalbuphine HCl, Form A (~155 mg) was completely dissolved in hexafluoroisopropanol (4 mL), and filtered via 0.2 micron nylon filter. The solution was allowed to evaporate to dryness in an open vial in a laboratory hood (approximate relative humidity 44% RH) at ambient temperature to yield Form D.

Example 25

Preparation of Nalbuphine HCl Form F

Nalbuphine HCl crystalline Form A was heated gradually and observed in situ using a VT-XRPD analyses. Crystalline Form F was obtained when the sample was heated (at 10° C./min) to 220° C., and remained unchanged upon cooling. Crystalline Form F was obtained at temperatures above 180° C.

Crystalline Form F was also obtained when nalbuphine HCl crystalline Form C, Form D, or a mixture of Forms I/H was heated to similar temperatures instead of Form A.

Example 26

Preparation of Nalbuphine HCl Form G

Nalbuphine HCl, Form A (~250 mg) was completely dissolved in methanol (1 mL) and filtered via 0.2 micron nylon filter. An aliquot of the solution (0.2 mL) was mixed with acetonitrile (5 mL) and the resulting clear solution was allowed to stand until precipitates appeared (after approximately 15 minutes). After one day, the solids were recovered by decanting the clear solution off, and drying under compressed air to yield Form G.

Example 27

Preparation of Nalbuphine HCl Form H

Nalbuphine HCl, Form A (~205 mg) was completely dissolved in methanol (0.75 mL) with an aid of ultrasonication and filtered via 0.2 micron nylon filter. An aliquot of the solution (0.15 mL) was mixed with ethyl acetate (1 mL), and precipitates were formed in the solution. The sample was allowed to stand overnight. The solids were recovered by decanting the solvent and the solid was air dried for using compressed air to yield a solid sample which consisted of mostly nalbuphine HCl Form H and small amount of Form C.

Example 28

Preparation of Nalbuphine HCl Form I

Nalbuphine HCl, Form A (~22 mg) was completely dissolved in methanol (0.2 mL) with the aid of ultra-sonication. The solution was allowed to evaporate to dryness in an open vial under nitrogen atmosphere (approximate relative humidity 17% RH) at ambient temperature to yield Form I.

Example 29

Preparation of Nalbuphine HCl Form K

Nalbuphine HCl, Form A (~26 mg) was completely dissolved in ethanol (4 mL) with the aid of ultra-sonication. The solution was allowed to evaporate to dryness in an open vial under nitrogen atmosphere (approximate relative humidity 17% RH) at ambient temperature to yield Form K.

Example 30

Preparation of Nalbuphine HCl Form U

Nalbuphine HCl, Form A (~200 mg) was dissolved in tert-butanol/water (6:4, v/v; 6 mL) to yield a slightly hazy solution which was filtered via 0.2 micron nylon filter to a clear solution. The solution was then frozen in a freezer (−22° C.) overnight and lyophilized overnight to yield dry solid, Form U.

Example 31

Preparation of Nalbuphine HCl Amorphous Form Z

Nalbuphine HCl, Form A (~203 mg) was completely dissolved in 2,2,2-trifluoroethanol (1 mL) and filtered via 0.2 micron nylon filter. The solution was allowed to evaporate to dryness in an open vial under nitrogen atmosphere (approximate relative humidity 17% RH) at ambient temperature to yield amorphous Form Z.

Example 32

Preparation of Nalbuphine HCl Amorphous Form Z

Nalbuphine HCl, Form A (~27 mg) was completely dissolved in 2-propanol (5 mL) with the aid of ultra-sonication and filtered via 0.2 micron nylon filter. The solution was allowed to evaporate to dryness in an open vial under nitrogen atmosphere (approximate relative humidity 17% RH) at ambient temperature to yield amorphous Form Z.

Example 33

Preparation of Nalbuphine HCl Amorphous Form Z

Nalbuphine HCl, Form A (~32 mg) was completely dissolved in 1-propanol (4 mL) with the aid of ultra-sonication and filtered via 0.2 micron nylon filter. The solution was allowed to evaporate to dryness in an open vial under nitrogen atmosphere (approximate relative humidity 17% RH) at ambient temperature to yield amorphous Form Z.

Example 34

Solid, Oral Dosage Form—Prophetic Example

As a specific embodiment of an oral composition, 100 mg of Form C of nalbuphine HCl, prepared as described herein, is formulated with sufficient finely divided lactose to provide a total amount of 580 to 590 mg to fill a size 0 hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A form of nalbuphine HCl selected from the group consisting of Form C, Form D, Form F, Form G, Form H, Form I, Form K, Form U and amorphous Form Z; wherein:
    Form C has PXRD °2θ peaks at about 9.76, about 15.22 and about 19.51;
    Form D has PXRD °2θ peaks at about 6.22, about 11.11, about 13.15 and about 14.89;
    Form F has PXRD °2θ peaks at about 7.89, about 12.9, about 14.22 and about 15.76;
    Form G has PXRD °2θ peaks at about 8.05, about 10.93, about 11.32, about 15.70 and about 17.41;
    Form H has PXRD °2θ peaks at about 11.23, about 15.37 and about 18.91;
    Form I has PXRD °2θ peaks at about 11.64, about 13.38, about 14.64 and about 15.57;
    Form K has PXRD °2θ peaks at about 10.98, about 11.58, about 13.35 and about 15.36;
    Form U has PXRD °2θ peaks at about 12.18, about 13.04, about 13.52 and about 19.04;
    and amorphous Form Z has a glass transition temperature of 48° C.

2. A form of nalbuphine HCl selected from the group consisting of Form C, Form D, Form F, Form G, Form H, Form I, Form K, Form U and amorphous Form Z; wherein:
    Form C has PXRD °2θ peaks at 9.76, 10.75, 12.37, 14.35, 15.22 and 16.27;
    Form D has PXRD °2θ peaks at 6.22, 11.11, 11.35, 11.77, 12.52 and 13.15;
    Form F has PXRD °2θ peaks at 7.89, 10.59, 11.73, 12.9, 14.22 and 15.75;
    Form G has PXRD °2θ peaks at 8.05, 10.93, 11.32, 12.55, 14.56 and 15.70;
    Form H has PXRD °2θ peaks at 11.23, 11.80, 12.52, 14.38, 15.37 and 18.10;
    Form I has PXRD °2θ peaks at 10.89, 11.64, 12.45, 13.38, 14.64 and 15.57;
    Form K has PXRD °2θ peaks at 10.98, 11.58, 12.42, 13.35, 15.36 and 15.99;
    Form U has PXRD °2θ peaks at 10.88, 12.18, 13.04, 13.52, 15.98 and 16.54; and
    amorphous Form Z has a glass transition temperature of 48° C.

3. A form of nalbuphine hydrochloride of claim 1, selected from the group consisting of Form C, Form D, Form F, Form G, Form H, Form I, Form K and Form U, wherein:
    Form C has PXRD peaks at °2θ at 12.37, 14.35, 16.27, 19.5, 21.25 and 24.19;
    Form D has PXRD peaks °2θ at 11.35, 11.77, 12.52, 13.15, 14.89, 16.87 and 22.45;
    Form F has PXRD peaks °2θ at 12.9, 14.22, 15.75, 19.77, 23.07 and 23.76;
    Form G has PXRD peaks °2θ at 8.05, 10.93, 11.32, 12.55, 15.70, 16.21, 17.41, 19.33 and 22.69;
    Form H has PXRD peaks °2θ at 11.23, 11.80, 12.52, 14.38, 18.10, 21.40 and 22.49;
    Form I has PXRD peaks °2θ at 10.89, 11.64, 12.45, 13.38, 15.57, 17.10, 19.95, 22.29 and 24.18;
    Form K has PXRD peaks °2θ at 11.58, 12.42, 15.36, 15.99, 17.13, 19.95 and 23.94; and
    Form U has PXRD peaks °2θ at 12.18, 13.04, 13.52, 16.54, 19.04, 21.26, 21.80, 22.08 and 24.16.

4. A form of nalbuphine HCl selected from the group consisting of Form F, Form G and Form U, as in claim 1, wherein, as measured by Differential Scanning Calorimetry (DSC):
    Form F is characterized by an endotherm at about 291° C.;
    Form G is characterized by an endotherm at about 293-296° C.; and
    Form U is characterized by an endotherm at about 290-293° C.

5. A form of nalbuphine HCl as in claim 1, which is about 90% to about 100% pure.

6. A form of nalbuphine HCl as in claim 1, which is about 98% to about 100% pure.

7. A pharmaceutical composition comprising a pharmaceutically acceptable carrier and a form of nalbuphine HCl as in claim 1.

8. A pharmaceutical composition made by mixing a form of nalbuphine HCl as in claim 1 and a pharmaceutically acceptable carrier.

9. A process for making a pharmaceutical composition comprising mixing a form of nalbuphine HCl as in claim 1 and a pharmaceutically acceptable carrier.

10. A method of providing an analgesic effect, comprising administering to a subject in need thereof, a therapeutically effective amount of a form of nalbuphine HCl as in claim 1.

11. A form of nalbuphine HCl as in claim 2, which is about 90% to about 100% pure.

12. A form of nalbuphine HCl as in claim 2, which is about 98% to about 100% pure.

13. A pharmaceutical composition comprising a pharmaceutically acceptable carrier and a form of nalbuphine HCl as in claim 2.

14. A pharmaceutical composition made by mixing a form of nalbuphine HCl as in claim 2 and a pharmaceutically acceptable carrier.

15. A process for making a pharmaceutical composition comprising mixing a form of nalbuphine HCl as in claim 2 and a pharmaceutically acceptable carrier.

16. A method of providing an analgesic effect, comprising administering to a subject in need thereof, a therapeutically effective amount of a form of nalbuphine HCl as in claim 2.

17. A form of nalbuphine HCl as in claim 4, which is about 90% to about 100% pure.

18. A form of nalbuphine HCl as in claim 4, which is about 98% to about 100% pure.

19. A pharmaceutical composition comprising a pharmaceutically acceptable carrier and a form of nalbuphine HCl as in claim 4.

20. A pharmaceutical composition made by mixing a form of nalbuphine HCl as in claim 4 and a pharmaceutically acceptable carrier.

21. A process for making a pharmaceutical composition comprising mixing a form of nalbuphine HCl as in claim 4 and a pharmaceutically acceptable carrier.

22. A method of providing an analgesic effect, comprising administering to a subject in need thereof, a therapeutically effective amount of a form of nalbuphine HCl as in claim 4.

* * * * *